United States Patent
Zhou et al.

(10) Patent No.: US 9,346,834 B2
(45) Date of Patent: May 24, 2016

(54) BORON-CONTAINING SMALL MOLECULES AS ANTIPROTOZOAL AGENTS

(75) Inventors: Huchen Zhou, Shanghai (CN); Dazhong Ding, Shaanxi (CN); Daoan Sun, Beijing (CN); Yasheen Zhou, Moraga, CA (US); Yong-Kang Zhang, San Jose, CA (US); Jacob J. Plattner, Orinda, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 115 days.

(21) Appl. No.: 13/503,016

(22) PCT Filed: Oct. 19, 2010

(86) PCT No.: PCT/US2010/053233
§ 371 (c)(1),
(2), (4) Date: Jun. 25, 2012

(87) PCT Pub. No.: WO2011/049971
PCT Pub. Date: Apr. 28, 2011

(65) Prior Publication Data
US 2012/0295875 A1   Nov. 22, 2012

Related U.S. Application Data

(60) Provisional application No. 61/253,376, filed on Oct. 20, 2009, provisional application No. 61/374,119, filed on Aug. 16, 2010.

(51) Int. Cl.
*C07F 5/02* (2006.01)

(52) U.S. Cl.
CPC ..................... *C07F 5/025* (2013.01)

(58) Field of Classification Search
None
See application file for complete search history.

(56) References Cited

U.S. PATENT DOCUMENTS

| | | | |
|---|---|---|---|
| 2,260,336 A | 10/1941 | Prescott et al. | |
| 3,686,398 A | 8/1972 | Kohn et al. | |
| 3,873,279 A | 3/1975 | Singer | |
| 4,602,011 A | 7/1986 | West et al. | |
| 4,716,035 A | 12/1987 | Sampathkamar | |
| 4,766,113 A | 8/1988 | West et al. | |
| 4,894,220 A | 1/1990 | Nabi et al. | |
| 4,919,934 A | 4/1990 | Deckner et al. | |
| 5,348,947 A | 9/1994 | Patel et al. | |
| 5,348,948 A | 9/1994 | Patel et al. | |
| 5,591,731 A | 1/1997 | Kennedy et al. | |
| 5,668,258 A | 9/1997 | Stolowitz | |
| 5,688,928 A | 11/1997 | Stolowitz | |
| 5,831,045 A | 11/1998 | Stolowitz et al. | |
| 5,880,188 A | 3/1999 | Austin et al. | |
| 5,962,498 A | 10/1999 | Driedger et al. | |
| 6,083,903 A | 7/2000 | Adams et al. | |
| 6,221,640 B1 | 4/2001 | Tao et al. | |
| 6,306,628 B1 | 10/2001 | Rothschild et al. | |
| 6,369,098 B1 | 4/2002 | Pershadsingh et al. | |
| 6,521,619 B2 | 2/2003 | Link et al. | |
| 6,800,645 B1 | 10/2004 | Cox et al. | |
| 6,855,848 B2 | 2/2005 | Scherer et al. | |
| 7,169,603 B2 | 1/2007 | Hedley et al. | |
| 7,205,425 B2 | 4/2007 | Shibasaki et al. | |
| 7,217,701 B2 | 5/2007 | Mikoshiba et al. | |
| 7,390,806 B2 | 6/2008 | Lee et al. | |
| 7,446,236 B2 | 11/2008 | Naud et al. | |
| 7,465,836 B2 | 12/2008 | Lee et al. | |
| 7,582,621 B2 | 9/2009 | Baker et al. | |
| 7,767,657 B2 | 8/2010 | Baker et al. | |
| 7,816,344 B2 | 10/2010 | Baker et al. | |
| 8,039,450 B2 | 10/2011 | Akama et al. | |
| 8,168,614 B2 | 5/2012 | Baker et al. | |
| 8,895,534 B2 * | 11/2014 | Baker et al. | 514/64 |
| 2002/0028831 A1 | 3/2002 | Manley | |
| 2002/0161230 A1 | 10/2002 | Meudt et al. | |
| 2003/0032673 A1 | 2/2003 | Nagy | |
| 2004/0077601 A1 | 4/2004 | Adams et al. | |
| 2004/0224923 A1 | 11/2004 | Lee et al. | |
| 2005/0054644 A1 | 3/2005 | Lee et al. | |
| 2005/0125852 A1 | 6/2005 | Caenepeel et al. | |
| 2006/0009386 A1 | 1/2006 | Stossel et al. | |
| 2006/0222671 A1 | 10/2006 | Weidner | |
| 2006/0234981 A1 | 10/2006 | Baker et al. | |
| 2007/0155699 A1 | 7/2007 | Baker et al. | |
| 2007/0286822 A1 | 12/2007 | Sanders et al. | |
| 2007/0293457 A1 | 12/2007 | Baker et al. | |
| 2009/0227541 A1 | 9/2009 | Baker et al. | |

(Continued)

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |

(Continued)

OTHER PUBLICATIONS

Database Registry Chemical Abstracts Service, Columbus, Ohio, Accession No. RN 1093643-69-6, Entered STN: Jan. 14, 2009.*

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anti-inflammatory agent (AN2728) for the potential topical treatment of psoriasis and atopic dernatitis", Bioorganic & Medicinal Chemistry Letters, (2009) 19: 2129-2132.

Alley, et al., "Recent Progress on Topical Therapy of Onychomycosis", Expert Opinion Investigate Drugs(Feb. 2007) 16(2): 157-67.

Austin, et al., "Oxaboroles and Salts and their Use of Biocides for Plastics", CAS, vol. 124, pp. 234-024, (1996).

(Continued)

*Primary Examiner* — Samantha Shterengarts
(74) *Attorney, Agent, or Firm* — Morgan, Lewis & Bockius LLP

(57) ABSTRACT

This invention provides, among other things, novel compounds useful for treating protozoal infections, pharmaceutical compositions containing such compounds, as well as combinations of these compounds with at least one additional therapeutically effective agent.

32 Claims, 2 Drawing Sheets

(56) References Cited

U.S. PATENT DOCUMENTS

| | | |
|---|---|---|
| 2010/0048570 A1 | 2/2010 | Kim et al. |
| 2010/0256092 A1 | 10/2010 | Xia et al. |

FOREIGN PATENT DOCUMENTS

| | | |
|---|---|---|
| WO | WO 9533754 | 5/1995 |
| WO | WO 9622023 A1 | 7/1996 |
| WO | WO 9812206 A1 | 3/1998 |
| WO | WO 0027822 | 5/2000 |
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Progress on New Therapeutics for Fungal Nail Infections", Annual Reports in Medicinal Chemistry, vol. 40: pp. 323-335, (2005).
Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Cusack, S., et al, "The 2 A Crystal Structure of leucyl-tRNA Synthetase and its Complex wish a Leucyl-Adenylate Analogue." EMBO Journal, vol. 19; pp. 2351-2361, (2000).
Dale, et al., "Substituted Styrenes VIII Syntheses and some Reactions of the Vinylbenzeneboronic Acids" J. Org. Chem. vol. 27; pp. 2598-2603, (Jan. 1, 1962).
Denis, "Pharmacology 1104 Lecture: Drug Classifications & Characteristics of Antimicrobials" (2003).
Dian, "International Nomenclature of Organics", China Petrochemical Press, 1st Edition; 50-51 (Jan. 21, 2004).
Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).
Ferrer, "Targeting Aminocytl-tRNA Synthetases for the Treatment of Fungal Infections", Drug News Perspective, vol. 19, No. 6; pp. 347-348, (Jul./Aug. 2006).
Fungicide: Definition from Answer.com, (1998).
Goodman, et al., "Goodman & Gilman's Manual of Pharmacology and Therapeutics" Chapter 40;681-694 (2008).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Sciences Press, vol. 16, No. 02; pp. 139-144, (1996) (ENGLISH ABSTRACT).
Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Arydialkkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).
Hui, et al., "In Vitro Penetration of a Novel Oxaborole Antifungal (AN2690) into the Human Nail Plate", Journal of Pharmaceutical Sciences (2007) 96(10): 2622-2631.
Lampe, et al., "Synthesis and Protien Kinase Inhibitory Activity of Balanol Analogues with Modified Benzophenone Subunits", J. Med. Chem., vol. 45(12); pp. 2624-2643, (2002).
Lee, K., et al., "Molecular Study of the Editing Active Site of Eschericaia coli Leucytl-tRNA Synthetase: Two Amino Acid Binding Site in the Editing Domain", vol. 54; pp. 693-704 (2004).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Luan, et al., "Inhibition of Experimental Periodontitis by a topical boron-base antimicrobial" J Dent. Res, 87(2):148-152 (2008).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from the 2-methylacrolein and triorganylboranes," Justus Liebigs Annalen Der Chemie, No. 06; pp. 1116-1134, (1976).
McMillin, et al., "Systemic Aspects of Psoriasis: An Integrative Model Based on Intestinal Etiology", Int. Med. vol. 2, Issue 2/3, (1999).
Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Mudran, "Drug Delivery to the Nail Following Topical Application", International Journal of Pharmaceutics, vol. 236: pp. 1-26, (2002).
Patani, et al., "Bioisosterism: A Rational Approach to Drug Design", Chem. Rev., vol. 96; pp. 3147-3176 (1996).
Perola, E., et al., "Successful Virtual Screening of a Chemical Database for Farnesltransferase Inhibitor Leads." vol. 43; pp. 401-4008, (2000).

(56) References Cited

OTHER PUBLICATIONS

Qin, et al., "Luminescent Organoboron Quinolate Polymers," Journal of the American Chemical Society, vol. 126, No. 22; pp. 7015-7018, (Jun. 9, 2004).
Qin, Clinical Mycology, Fudan Press, Shanghai Medical University Press, pp. 92, 111, 340-41, 365, 437 and 487 (2001) With English Translation.
Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).
Silverman, "The Organic Chemistry of Drug Design and Drug Action", 2nd Edition, Northwestern University, Department of Chemistry, Evanston, Illinois, Section 2: 29-32 (2004).
Snyder, et al. "Common Bacteria Whose Susceptibility to Antimicrobials in no longer Predictable" J. Med. Liban, vol. 48 No. 4; pp. 208-214, (2000).
Sugar, et al., "Comparison of Three Methods of Antifungal Susceptibility Testing with the Proposed NCCLS Standard Broth Macrodilution Assay: Lack of Effect of Phenol Red" Diagn, Microbiol. Infect. Dis. vol. 21; pp. 129-133, (1995).
Tabuchi, et al., "Anticoccidial Activity of some Azacyclo Organoborinates," Heterocycles, vol. 60, No. 01; pp. 177-182, (2003).
Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).
Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).
Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).
Tschampel, et al., "Arylboronic Acids. VII. Some Reactions to o-Formybenzeneboronic Acids", J. Org. Chem. vol. 29, No. 8; pp. 2168-2172, (1964).
Turner, et al., Current Pharmaceutical Design, vol. 2; pp. 209-224 (1996).
Vippagunta, "Crystalline Solids", Advanced Drug Delivery Reviews, vol. 48; pp. 3-26, (2001).
Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).
Ye, et al., "Convenient and Versatile Syntheis of formyl-substituted Benzoxaboroles", Tetrahedron, vol. 65; pp. 8738-8744, (2009).
Williams, et al., "Foye's Principles of Medicinal Chemistry", 5th Edition, 2002, Lippincoot Williams & Wilkins, p. 59.
Zhdankin, et al., "Synthesis and Structure of Benzoboroxoles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).
Zhou, et al., "Pattern Recognition of Proteins Based on an Array of Functionalized Porphyrins," J. Am. Chem. Soc., 128:2421-2425 (2006).
Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (ENGLISH ABSTRACT).
"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.
"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.
"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.
"AN2718 Demonstrates Significant Efficacy in Three Phase Ib Psoriasis Microplaque Trials" Scientific Presentation at the American Academy of Dermatology Annual Meeting, San Francisco, CA Mar. 6-10, 2009.
"AN2728 Demonstrates Significant Safety and Efficacy in Phase IIa Double Blind Trial in Plaque Type Psoriasis", Scientific Presentation at the American Academy of Dermatology Annual Meeting, San Francisco, CA Mar. 6-10, 2009.
"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.
"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.
"AN2920, A Novel Oxaborole, Shows in Vitro and in Vivo Activity Against *Trypanosomal brucei*", Scientific Presentation at the American Society of Tropical Medicine and Hygiene Conference, New Orleans, LA Dec. 7-11, 2008.
"A Novel Oxaborole, AN3520, Show Efficacy against Human African Trypanomiasis in Vitro and in Vivo, Including Promise in a Murine CNS Model of *T. brucei* Infection", Scientific Presentation at the American Society of Tropical Medicine and Hygiene Conference, New Orleans, LA Dec. 7-11, 2008.
"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.
"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.
"PreclinicalToxicology of AN2728, a Novel Oxaborole in Devleopment for the Topical Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.
"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.
"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Results of in Vivo Efficacy and Preclinical Safety Studies", Scientific Presentation at the International Investigative Dermatology Conference, Kyoto, Japan, May 14-18, 2008.
"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.
"Preclinical Toxicology of AN2728, a Novel Borinic Acid Ester with Anti-Inflammatory Activity", American Academy of Dermatology, 65th Annual Meeting, Washington, DC, Feb. 2-6, 2007.
"AN2728, a Novel Oxaborole with Broad-Spectrum in Vitro Anti-Inflammatory Activity", American Academy of Dermatology, 65th Annual Meeting, Washington, DC, Feb. 2-6, 2007.

(56) References Cited

OTHER PUBLICATIONS

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.

"Skin Penetration and Anti-Inflammatory Activity of AN2728, a novel Oxaborole", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the Ameican Associate of Pharmaceutucal Scientists, Annual Meeting, San Antonio, TX, Oct. 29-Nov. 2, 2006.

Akama, et al., "Discovery of Novel Boron Containing Compounds as Dual Inhibitors of TNF-α and IL-23 Release", World Congress of Inflammation, Tokyo, Japan, Jul. 6-10, 2009.

Akama, et al., "Novel Boron-Containing Small Molecules Demonstrate Potent Activity Against Trypanosoma cruzi", The XIIth International Congress of Parasitology, Melbourne, Australia, Aug. 15-20, 2010.

Akama, et al., "Structure-activity studies of AN2728 and AN2898, novel compounds with anti-inflammatory activity", International Investigative Dermatology Conference, Kyoto, Japan, May 14-18, 2008.

Akama, et al., "Structure-Activity Studies of Novel Oxaborole Dual Inhibitors of PDE4 and IL-23 Release", Society for Investigative Dermatology Annual Meeting, Montreal, Canada, May 6-9, 2009.

Baker, et al., "Therapeutic potential of boron-containing compounds", Future Med. Chem (2009), 1275-1288.

Chen, et al., "Lead Optimization Investigation of Oxaboroles for the Treatment of Human African Trypanosomiasis", American Chemical Society, Washington, DC, Aug. 16-20, 2009.

Ding, et al., "Synthesis and biological evaluations of P4-benzoxaborole-substituted macrocyclic inhibitors of HCV NS3 protease", Bioorganic & Medicinal Chemistry Letters 20 (2010), 7317-7322.

Ding et al., "Discovery of Novel Benzoxaborole-Based Potent Antitrypanosomal Agents", Medicianl Chemistry Letters (2010), 1, 165-169.

Freund, et al., "Novel Boron-Containing Small Molecules as Potential Therapeutics Against Human Lymphatic Filariasis", The American Society of Tropical Medicine and Hygiene, Washington, DC, Nov. 20, 2009.

Freund, et al., "Novel Boron-Containing Small Molecules Demonstrate Potent Activity Against Malaria Parasites with Excellent Drug-like Properties", The American Society of Tropical Medicine and Hygiene, Washington, DC, Nov. 20, 2009.

Hernandez, et al., "Discovery and Mechanism of Action of AN3365: A Novel Boron-containing Antibacterial Agent in Clinical Development for Gram-negative Infections", 2010 Interscience Conference on Antimicrobial Agents and Chemotherapy, Boston, MA, Sep. 12-15, 2010.

Jacobs et al., "Novel Oxaborole 6-Carboxamides Demonstrate Potential for Treatment of CNS-Stage Human African Trypanosomiasis", Key Stone Symposium, Breckenridge, CO, Mar. 22-26, 2009.

Jarnagin, et al., "AN6415: A Novel, Highly Potent, PDE4 Inhibitor with Oral Activity and Broad Spectrum Cytokine Suppression", 8th Annual Cytokines and Inflammation Conference, La Jolla, CA, Jan. 28-29, 2010.

Jarnagin, et al., "A Series of Potent Orally-Available Benzoxaborole PDE4 Inhibitors which Gain Potency by use of Novel Contacts Within the PDE4 Active Site", Gordon Conference on Cyclic Nucleotide Phosphodiesterases, Waterville Valley, NH, Jun. 13-18, 2010.

Li, et al., "Synthesis of new acylsulfamoyl benzoxaboroles as potent inhibitors of HCV NS3 protease", Bioorganic & Medicinal Chemistry Letters 20 (2010), 7493-7497.

Nare, et al., "Discovery of Novel Orally Bioavailable Oxaborole 6-Carboxamides That Demonstrate Cure in a Murine Model of Late-Stage Central Nervous System African Trypanosomiasis", Antimicrobial Agents and Chemotherapy, Oct. 2010, p. 4379-4388.

Seiradake et al., "Crystal Structures of the Human and Fungal Cytosolic Leucyl-tRNA Synthetase Editing Domains: A Structural Basis for the Rational Design of Antifungal Benzoxaboroles", J. Mol. Biol. (2009) 390, 196-207.

Xia, et al., "Discovery of Novel Benzoxaboroles as a New Class of b-Lactamase Inhibitors", 8th Annual Congress of International Drug Discovery Science and Technology, Beijing, China, Oct. 23-26, 2010.

Zhang, et al., "Design and synthesis of boron-containing PDE4 inhibitors using soft-drug strategy for potential dermatologic anti-inflammatory application", Biorganic & Medicinal Chemistry Letters 20, (2010), 2270-2274.

Zhang, et al., "Synthesis and structure—activity relationships of novel benzoxaboroles as a new class of antimalarial agents", Biorganic & Medicinal Chemistry Letters 21, (2011), 644-651.

"AN2718 has Broad Spectrum Antifungal Activity Necessary for the Topical Treatment of Skin and Nail Fungal Infections", The American Academy of Dermatology Annual Meeting, San Francisco, CA, Mar. 6-10, 2009.

"AN2728 Demonstrates Significant Efficacy in Three Phase Ib Psoriasis Microplaque Trials", The American Academy of Dermatology Annual Meeting, San Francisco, CA, Mar. 6-10, 2009.

"Boron and non-boron HCV NS3/4 protease inhibitors: new motifs with high potency against PI-resistant mutants", HCV Drug Discovery, 5th CHI Conference, San Diego, CA, Apr. 28-29, 2010.

"Novel Cyclic Boronates as HCV NS3/4A Protease Inhibitors", 7th Annual Congress of International Drug Discovery Science and Technology, Shanghai, China, Oct. 22-25, 2009.

"Structure-Guided Discovery of (S)-3-(aminomethyl)benzo[c][1,2]oxaborol-1(3H)-ol hydrochloride (ABX): A First in Class Gram-negative Antibacterial", Anti-Infectives Summit, Philadelphia, PA, Jan. 25-27, 2010.

* cited by examiner

| Compound Number | T. b. brucei S427 IC50 ug/mL | T.b.brucei STIB795 IC50 µM | T. cruzi CL2 IC50 µM | T.b.rhodesiense STIB900 IC50 µM | L. infantum IC50 µM | T. brucei LeuRS IC50 µM | P. falciparum IC50 µM |
|---|---|---|---|---|---|---|---|
| H178 | 1.62 | 2.04 | >64 | 2.61 | >64 | 30.6 | |
| H179 | 4.47 | 6.68 | 13.23 | 8.88 | >64 | 272.8 | |
| H180 | 3.53 | 7.46 | 54.47 | 7.76 | >64 | >100 | |
| H181 | 1.3 | 0.62 | >32 | 0.94 | >64 | | |
| H182 | 0.159 | | | | | | |
| H183 | 0.637 | 3.45 | >64 | 5.49 | >64 | 13.03 | |
| H184 | 1.76 | 5.44 | >64 | 6.96 | >64 | 30.93 | |
| H185 | 1.68 | | | | | 15.81 | |
| H186 | 0.145 | | | | | | |
| H187 | 2.81 | 1.13 | >32 | 1.11 | >64 | 54.29 | |
| H188 | 0.45 | <0.32 | 10.62 | 0.44 | >64 | | |
| H189 | 1.49 | 0.85 | 15.16 | 0.9 | >64 | | |
| H190 | 0.746 | 0.45 | >32 | 0.81 | >64 | | |
| H191 | 2.79 | 1.15 | >32 | 1.15 | >64 | 77.66 | |
| H192 | 0.62 | 0.54 | 24.66 | 0.9 | >64 | | |
| H193 | 1.68 | 1.12 | >32 | 0.88 | >64 | 159.8 | |
| H194 | 2.07 | 4.84 | 32.69 | 7.65 | 57.02 | | |
| H195 | 0.305 | <0.32 | 10.25 | <0.32 | 43.6 | | |
| H196 | >5 | 2.48 | >32 | 5.3 | >64 | 113.2 | |
| H197 | 2.64 | 6.89 | >32 | 8.26 | >64 | 71.31 | |
| H198 | 2.06 | <0.32 | 11.34 | 0.45 | >64 | 104.3 | 0.16 |
| H199 | 0.273 | 0.81 | 1.04 | <0.32 | 4.4 | 3.61 | |
| H200 | 0.17 | 0.36 | 1.09 | <0.32 | 20.48 | 3.54 | |
| H201 | 0.69 | 0.46 | >32 | 0.87 | >64 | 7.41 | |
| H202 | 2.3 | 2.04 | 8.06 | 2.27 | >64 | 117.4 | |
| H203 | 0.748 | | | | | 2.775 | |
| H204 | 2.99 | | | | | 1.55 | |
| H205 | 1.45 | | | | | 2.09 | |
| H206 | 2.37 | | | | | 41.71 | |
| H207 | 2.07 | | | | | 27.17 | |
| H208 | 2.26 | | | | | 30.81 | |
| H209 | 1.22 | | | | | | |
| H210 | 0.455 | | | | | 3.84 | |
| H211 | 1.93 | | | | | 2.48 | |
| H212 | 0.884 | | | | | 3.48 | |
| H213 | 0.71 | | | | | 31.35 | |

Figure 1

| Compound Number | T. b. brucei S427 IC50 ug/mL | T.b.brucei STIB795 IC50 µM | T. cruzi CL2 IC50 µM | T.b.rhodesiense STIB900 IC50 µM | L. infantum IC50 µM | T. brucei LeuRS IC50 µM | P. falciparum IC50 µM |
|---|---|---|---|---|---|---|---|
| H214 | 3.39 | | | | | 2.89 | |
| H215 | 0.68 | | | | | 4.74 | |
| H216 | 0.086 | | | | | 5.01 | |
| H217 | 1.99 | | | | | 284.9 | |
| H218 | 0.572 | 0.73 | >32 | 0.62 | >64 | >100 | |

Figure 1 Con.

BORON-CONTAINING SMALL MOLECULES AS ANTIPROTOZOAL AGENTS

CROSS-REFERENCE TO RELATED APPLICATIONS

This application claims priority to PCT Patent Application No. PCT/US10/53233, filed Oct. 19, 2010, which claims the benefit of U.S. Provisional Pat. App. No. 61/253,376, filed Oct. 20, 2009, and U.S. Provisional Pat. App. No. 61/374,119, filed Aug. 16, 2010, each of which is incorporated by reference in its entirety for all purposes.

BACKGROUND OF THE INVENTION

The global rise of protozoa resistant to antimicrobials in general, poses a major threat. Deployment of massive quantities of antimicrobial agents into the exosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multidrug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

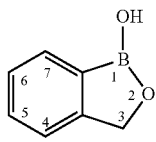

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutically effective agent.

BRIEF DESCRIPTION OF THE DRAWING

Biological data for exemplary compounds of the invention is provided in FIG. 1.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato) diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2$ (pddf) is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-Ph$SO_2$Cl is 3-fluoro-4-nitrophenylsulfonyl chloride; 2-MeO-4-$NO_2$-Ph$SO_2$Cl is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR''''—C(NR'R"R''')=NR"'', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2 m'+1), where m' is the total number of carbon atoms in such radical. R', R", R'", R'''' and R''''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R'''' and R''''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R'''' and R''''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted $C_1$ or $C_2$ or $C_3$ or $C_4$ or $C_5$ or $C_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective,"

"pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine or d-lysine or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy,* 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term anti-protozoal or anti-protozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The invention provides novel boron compounds. The novel compounds, as well as pharmaceutical compositions containing such compounds or combinations of these compounds with at least one additional therapeutically effective agent, can be used for, among other things, treating protozoal infections.

III. The Compounds
III. a) Cyclic Boronic Esters

In one aspect, the invention provides a compound of the invention. In an exemplary embodiment, the invention is a compound described herein. In an exemplary embodiment, the invention is a compound according to a formula described herein.

In an exemplary embodiment, the compound of the invention is

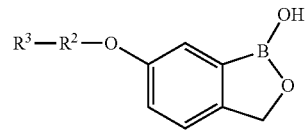

or a salt, hydrate, or solvate thereof wherein $R^2$ is selected from the group consisting of unsubstituted linear alkylene, alkylene substituted with unsubstituted alkyl, alkylene substituted with unsubstituted aryl, and $R^3$ is selected from the group consisting of unsubstituted alkyl, halosubstituted alkyl, unsubstituted cycloalkyl, halosubstituted or unsubstituted heteroaryl, vinyl, hydroxy substituted alkyl, —C(O)H, —C(O)$R^{12}$, —C(O)O$R^{13}$, C(O)NH$R^{14}$, —O$R^{10}$ and —NH$R^{11}$ wherein $R^{12}$ is unsubstituted alkyl; $R^{13}$ is selected from the group consisting of H, unsubstituted alkyl, unsubstituted alkoxy methyl; $R^{14}$ is selected from the group consisting of H, unsubstituted alkyl, unsubstitutedalkyl substituted aryl; and $R^{10}$ is selected from the group consisting of H, unsubstituted alkyl, unsubstituted heterocycloalkyl, $R^{11}$ is selected from the group consisting of C(O)O$R^{20}$, wherein $R^{20}$ is unsubstituted alkyl.

In an exemplary embodiment, the compound of the invention has the following structure:

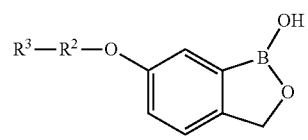

wherein $R^2$ is selected from the group consisting of unsubstituted linear alkylene, alkylene substituted with unsubstituted alkyl, alkylene substituted with unsubstituted aryl, and $R^3$ is selected from the group consisting of halosubstituted alkyl, unsubstituted cycloalkyl, halosubstituted or unsubstituted heteroaryl, vinyl, hydroxy substituted alkyl, —C(O)H, —C(O)$R^{12}$, —C(O)O$R^{13}$, C(O)NH$R^{14}$, —O$R^{10}$ and —NH$R^{11}$ wherein $R^{12}$ is unsubstituted alkyl; $R^{13}$ is selected from the group consisting of H, unsubstituted alkyl, unsubstituted alkoxy methyl; $R^{14}$ is selected from the group consisting of H, unsubstituted alkyl, unsubstitutedalkyl substituted aryl; and $R^{10}$ is selected from the group consisting of H, unsubstituted alkyl, unsubstituted heterocycloalkyl, $R^{11}$ is selected from the group consisting of C(O)O$R^{20}$, wherein $R^{20}$ is unsubstituted alkyl.

In an exemplary embodiment, the compound of the invention is

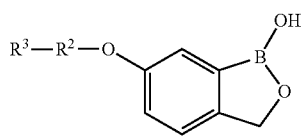

or a salt thereof wherein $R^2$ is selected from the group consisting of unsubstituted linear alkylene, alkylene substituted with unsubstituted alkyl, alkylene substituted with unsubstituted aryl, and $R^3$ is —C(O)O$R^{13}$; $R^{13}$ is selected from the group consisting of H, unsubstituted alkyl and unsubstituted alkoxy methyl. In an exemplary embodiment, $R^2$ is selected from the group consisting of unsubstituted linear alkylene, alkylene substituted with unsubstituted alkyl, alkylene substituted with unsubstituted aryl, and $R^3$ is —C(O)OH.

In an exemplary embodiment, the compound of the invention has the following structure:

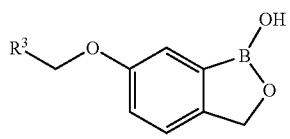

wherein $R^3$ is as described herein. In an exemplary embodiment, $R^3$ is —COOH.

In an exemplary embodiment, the compound of the invention has the following structure:

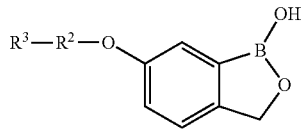

wherein $R^2$ is unsubstituted linear alkylene, $R^3$ is as described herein. In an exemplary embodiment, $R^2$ is as described herein and $R^3$ is —COOH.

In an exemplary embodiment, the compound of the invention has the following structure:

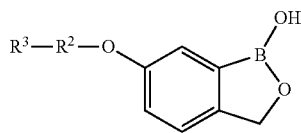

wherein $R^2$ is unsubstituted linear alkylene, alkylene substituted with unsubstituted alkyl, alkylene substituted with unsubstituted aryl, and $R^3$ is as described herein. In an exemplary embodiment, the compound of the invention has the following structure:

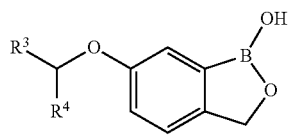

wherein $R^3$ is as described herein and $R^4$ is $C_1$-$C_6$ unsubstituted alkyl. In an exemplary embodiment, $R^3$ is as described herein and $R^4$ is methyl. In an exemplary embodiment, $R^3$ is as described herein and $R^4$ is ethyl. In an exemplary embodiment, $R^3$ is as described herein and $R^4$ is propyl. In an exemplary embodiment, $R^3$ is as described herein and $R^4$ is isopropyl. In an exemplary embodiment, $R^3$ is as described herein and $R^4$ is $C_4$ unsubstituted alkyl. In an exemplary embodiment, $R^3$ is as described herein and $R^5$ is $C_6$ unsubstituted alkyl. In an exemplary embodiment, $R^3$ is as described herein and $R^4$ is $C_6$ unsubstituted alkyl. In an exemplary embodiment, $R^2$ is as described herein and $R^3$ is —COOH.

In an exemplary embodiment, the compound of the invention has the following structure:

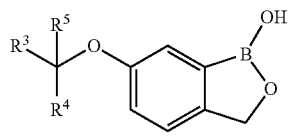

wherein $R^4$ is $C_1$-$C_6$ unsubstituted alkyl and $R^5$ is $C_1$-$C_6$ unsubstituted alkyl. In an exemplary embodiment, $R^4$ is methyl and $R^5$ is methyl. In an exemplary embodiment, $R^4$ is ethyl and $R^5$ is methyl. In an exemplary embodiment, $R^4$ is propyl and $R^5$ is methyl. In an exemplary embodiment, $R^4$ is isopropyl and $R^5$ is methyl. In an exemplary embodiment, $R^4$ is $C_4$ unsubstituted alkyl and $R^5$ is methyl. In an exemplary embodiment, $R^4$ is $C_6$ unsubstituted alkyl and $R^5$ is methyl. In an exemplary embodiment, $R^4$ is $C_6$ unsubstituted alkyl and $R^5$ is methyl. In an exemplary embodiment, $R^2$ is as described herein and $R^3$ is —COOH.

In an exemplary embodiment, the compound of the invention has the following structure:

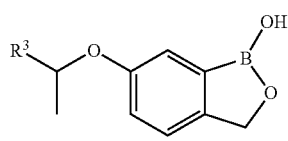

wherein $R^3$ is as described herein. In an exemplary embodiment, $R^3$ is —COOH.

In an exemplary embodiment, the compound of the invention has the following structure:

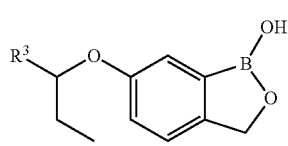

wherein $R^3$ is as described herein. In an exemplary embodiment, $R^2$ is as described herein and $R^3$ is —COOH.

In an exemplary embodiment, the compound of the invention has the following structure:

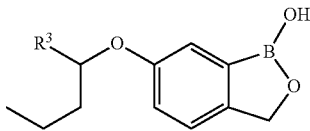

wherein $R^3$ is as described herein. In an exemplary embodiment, $R^2$ is as described herein and $R^3$ is —COOH.

In an exemplary embodiment, the compound of the invention has the following structure:

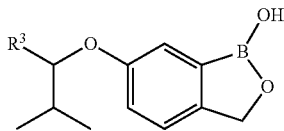

wherein $R^3$ is as described herein. In an exemplary embodiment, $R^2$ is as described herein and $R^3$ is —COOH.

In an exemplary embodiment, the compound of the invention has the following structure:

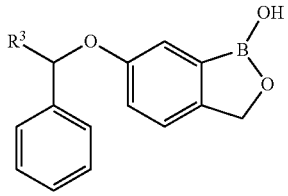

wherein $R^3$ is as described herein. In an exemplary embodiment, $R^2$ is as described herein and $R^3$ is —COOH.

In an exemplary embodiment, the compound of the invention has the following structure:

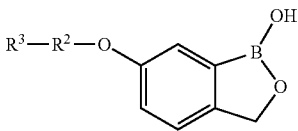

wherein $R^2$ is as described herein, and $R^3$ is selected from the group consisting of halosubstituted aryl, cycloalkyl, substituted or unsubstituted heteroaryl, —C(O)H, —C(O)OR$^{13}$, —C(O)NHR$^{14}$, wherein $R^{13}$ is H or unsubstituted alkyl; $R^{14}$ is selected from the group consisting of H, unsubstituted alkyl, substituted and unsubstituted arylalkyl and unsubstituted cycloalkyl. In an exemplary embodiment, $R^{13}$ is unsubstituted $C_1$-$C_6$ alkyl. In an exemplary embodiment, $R^{13}$ is unsubstituted $C_2$ alkyl.

In an exemplary embodiment, $R^2$ is unsubstituted linear alkylene, and $R^3$ is selected from the group consisting of halosubstituted aryl, cycloalkyl, substituted or unsubstituted heteroaryl, —C(O)H, —C(O)OR$^{13}$, —C(O)NHR$^{14}$, wherein $R^{13}$ is H or unsubstituted alkyl; $R^{14}$ is selected from the group consisting of H, unsubstituted alkyl, substituted and unsubstituted arylalkyl and unsubstituted cycloalkyl. In an exemplary embodiment, $R^2$ is methylene, and $R^3$ is selected from the group consisting of halosubstituted aryl, cycloalkyl, substituted or unsubstituted heteroaryl, —C(O)H, —C(O)OR$^{13}$, —C(O)NHR$^{14}$, wherein $R^{13}$ is H or unsubstituted alkyl; $R^{14}$ is selected from the group consisting of H, unsubstituted alkyl, substituted and unsubstituted arylalkyl and unsubstituted cycloalkyl. In an exemplary embodiment, $R^2$ is unsubstituted linear alkylene and $R^3$ is —COOH.

In an exemplary embodiment, $R^2$ is as described herein, and $R^3$ is —OR$^{10}$, wherein $R^{10}$ is selected from the group consisting of H, unsubstituted alkyl and unsubstituted heterocycloalkyl. In an exemplary embodiment, $R^2$ is unsubstituted linear alkylene and $R^3$ is —OR$^{10}$, wherein $R^{10}$ is selected from the group consisting of H, unsubstituted alkyl and unsubstituted heterocycloalkyl. In an exemplary embodiment, $R^2$ is methylene and $R^3$ is —OR$^{10}$, wherein $R^{10}$ is selected from the group consisting of H, unsubstituted alkyl and unsubstituted heterocycloalkyl. In an exemplary embodiment, $R^2$ is methylene and $R^3$ is —OH. In an exemplary embodiment, $R^2$ is methylene and $R^3$ is —OR$^{10}$, wherein $R^{10}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^2$ is methylene and $R^3$ is —OR$^{10}$, wherein $R^{10}$ is unsubstituted heterocycloalkyl. In an exemplary embodiment, $R^2$ is methylene and $R^3$ is —OR$^{10}$, wherein $R^{10}$ is tetrahydropyranyl.

In an exemplary embodiment, $R^2$ is as described herein, and R is —NHR$^{11}$, wherein $R^{11}$ is selected from the group consisting of C(O)OR$^{20}$, wherein $R^{20}$ is H or unsubstituted alkyl. In an exemplary embodiment, $R^2$ is unsubstituted linear alkylene and $R^3$ is —NHR$^{11}$, wherein $R^{11}$ is selected from the group consisting of C(O)OR$^{20}$, wherein $R^{20}$ is unsubstituted alkyl. In an exemplary embodiment, $R^2$ is methylene and $R^3$ is —NHR$^{11}$, wherein $R^{11}$ is selected from the group consisting of C(O)OR$^{20}$, wherein $R^{20}$ is unsubstituted alkyl. In an exemplary embodiment, for any of the embodiments in this paragraph, $R^{20}$ is H. In an exemplary embodiment, for any of the embodiments in this paragraph, $R^{20}$ is methyl. In an exemplary embodiment, for any of the embodiments in this paragraph, $R^{20}$ is ethyl. In an exemplary embodiment, for any of the embodiments in this paragraph, $R^{20}$ is unsubstituted $C_3$ alkyl. In an exemplary embodiment, for any of the embodiments in this paragraph, $R^{20}$ is unsubstituted $C_4$ alkyl. In an exemplary embodiment, for any of the embodiments in this paragraph, $R^{20}$ is t-butyl. In an exemplary embodiment, for any of the embodiments in this paragraph, $R^{20}$ is unsubstituted $C_5$ alkyl. In an exemplary embodiment, for any of the embodiments in this paragraph, $R^{20}$ is unsubstituted $C_6$ alkyl.

In an exemplary embodiment, $R^2$ is as described herein, and $R^3$ is —C(O)H. In an exemplary embodiment, $R^2$ is unsubstituted linear alkylene and $R^3$ is —C(O)H. In an exemplary embodiment, $R^2$ is methylene and $R^3$ is —C(O)H.

In an exemplary embodiment, $R^2$ is as described herein, and $R^3$ is —C(O)R$^{12}$, $R^{12}$ is unsubstituted alkyl. In an exemplary embodiment, $R^2$ is C(O)—, unsubstituted linear alkylene and $R^3$ is —C(O)R$^{12}$ is unsubstituted alkyl. In an exemplary embodiment, $R^2$ is methylene and $R^3$ is —C(O)R$^{12}$.

In an exemplary embodiment, the compound of the invention has the following structure:

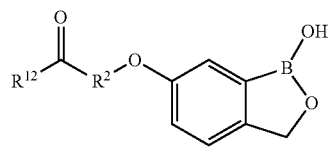

wherein $R^2$ and $R^{12}$ are each as described herein. In an exemplary embodiment, $R^2$ is as described herein and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^2$ is methylene or ethylene or propylene or butylene or pentylene or hexylene and $R^{12}$ is as described herein. In an exemplary embodiment, $R^2$ is methylene and $R^{12}$ is methyl or ethyl or unsubstituted $C_3$ alkyl or unsubstituted $C_4$ alkyl. In an exemplary embodiment, $R^2$ is ethylene and $R^{12}$ is methyl or ethyl or unsubstituted $C_3$ alkyl or unsubstituted $C_4$ alkyl. In an exemplary embodiment, $R^2$ is propylene and $R^{12}$ is methyl or ethyl or unsubstituted $C_3$ alkyl or unsubstituted $C_4$ alkyl. In an exemplary embodiment, $R^2$ is unsubstituted linear alkylene and $R^{12}$ is —OH.

In an exemplary embodiment, the compound of the invention has the following structure:

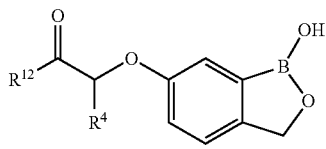

wherein $R^4$ and $R^{12}$ are each as described herein. In an exemplary embodiment, $R^4$ is as described herein and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is methyl or ethyl or unsubstituted $C_3$ alkyl or unsubstituted $C_4$ alkyl or unsubstituted $C_5$ alkyl or unsubstituted $C_6$ alkyl and $R^{12}$ is as described herein. In an exemplary embodiment, $R^4$ is methyl and $R^{12}$ is methyl or ethyl or unsubstituted $C_3$ alkyl or unsubstituted $C_4$ alkyl. In an exemplary embodiment, $R^4$ is ethyl and $R^{12}$ is methyl or ethyl or unsubstituted $C_3$ alkyl or unsubstituted $C_4$ alkyl. In an exemplary embodiment, $R^4$ is propyl and $R^{12}$ is methyl or ethyl or unsubstituted $C_3$ alkyl or unsubstituted $C_4$ alkyl. In an exemplary embodiment, $R^4$ is isopropyl and $R^{12}$ is methyl or ethyl or unsubstituted $C_3$ alkyl or unsubstituted $C_4$ alkyl. In an exemplary embodiment, $R^4$ is as described herein, and $R^{12}$ is —OH.

In an exemplary embodiment, the compound of the invention has the following structure:

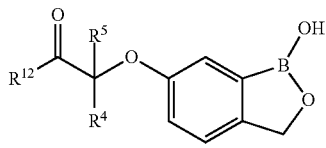

wherein $R^4$, $R^5$ and $R^{12}$ are each as described herein. In an exemplary embodiment, $R^4$ and $R^5$ are each as described herein and $R^{12}$ is methyl or ethyl or unsubstituted $C_3$ alkyl. In an exemplary embodiment, $R^4$ is methyl, $R^5$ is as described herein and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is ethyl, $R^5$ is as described herein and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is unsubstituted $C_3$ alkyl, $R^5$ is as described herein and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is methyl, $R^5$ is methyl and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is methyl, $R^5$ is methyl and $R^{12}$ is methyl or ethyl or unsubstituted $C_3$ alkyl. In an exemplary embodiment, $R^4$ is ethyl, $R^5$ is ethyl and $R^{12}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ and $R^5$ are as described herein, and $R^{12}$ is —OH.

In an exemplary embodiment, $R^2$ is as described herein, and $R^3$ is —C(O)OR$^{13}$, wherein $R^{13}$ is H or unsubstituted $C_1$ or $C_2$ or $C_3$ or $C_4$ or $C_5$ or $C_6$ alkyl. In an exemplary embodiment, $R^2$ is unsubstituted linear alkylene, and $R^3$ is —C(O)OR$^{13}$, wherein $R^{13}$ is H or unsubstituted $C_1$ or $C_2$ or $C_3$ or $C_4$ or $C_5$ or $C_6$ alkyl. In an exemplary embodiment, $R^2$ is methylene and $R^3$ is —C(O)OR$^{13}$, wherein $R^{13}$ is H or unsubstituted $C_1$ or $C_2$ or $C_3$ or $C_4$ or $C_5$ or $C_6$ alkyl. In an exemplary embodiment, $R^{13}$ is H or unsubstituted $C_1$ or $C_2$ or $C_4$ alkyl. In an exemplary embodiment, $R^{13}$ is H, methyl, ethyl or tert-butyl. In an exemplary embodiment, $R^2$ is methylene and $R^{13}$ is H. In an exemplary embodiment, $R^2$ is methylene and $R^{13}$ is ethyl. In an exemplary embodiment, $R^2$ is methylene and $R^{13}$ is tert-butyl. In an exemplary embodiment, $R^2$ is methylene and $R^{13}$ is methyl.

In an exemplary embodiment, the compound of the invention has the following structure:

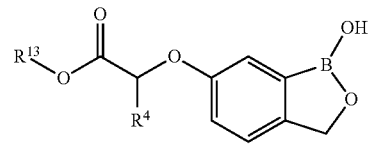

wherein $R^4$ and $R^{13}$ are each as described herein. In an exemplary embodiment, $R^4$ is as described herein and $R^{13}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is methyl or ethyl or unsubstituted $C_3$ alkyl or unsubstituted $C_4$ alkyl or unsubstituted $C_5$ alkyl or unsubstituted $C_6$ alkyl and $R^{13}$ is as described herein. In an exemplary embodiment, $R^4$ is methyl and $R^{13}$ is methyl or ethyl or unsubstituted $C_3$ alkyl or unsubstituted $C_4$ alkyl. In an exemplary embodiment, $R^4$ is ethyl and $R^{13}$ is methyl or ethyl or unsubstituted $C_3$ alkyl or unsubstituted $C_4$ alkyl. In an exemplary embodiment, $R^4$ is propyl and $R^{13}$ is methyl or ethyl or unsubstituted $C_3$ alkyl or unsubstituted $C_4$ alkyl. In an exemplary embodiment, $R^4$ is isopropyl and $R^{13}$ is methyl or ethyl or unsubstituted $C_3$ alkyl or unsubstituted $C_4$ alkyl. In an exemplary embodiment, $R^4$ is as described herein and $R^{13}$ is H.

In an exemplary embodiment, the compound of the invention has the following structure:

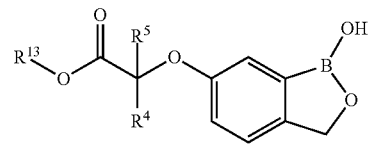

wherein $R^4$, $R^5$ and $R^{13}$ are each as described herein. In an exemplary embodiment, $R^4$ is methyl, $R^5$ is methyl and $R^{13}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^4$ is methyl, $R^5$ is methyl and $R^{13}$ is methyl or ethyl or unsubstituted $C_3$ alkyl. In an exemplary embodiment, $R^4$ and $R^5$ are as described herein, and $R^{13}$ is H.

In an exemplary embodiment, $R^2$ is as described herein, and $R^3$ is unsubstituted cycloalkyl. In an exemplary embodiment, $R^2$ is unsubstituted linear alkylene, and $R^3$ is unsubstituted cycloalkyl. In an exemplary embodiment, $R^2$ is unsubstituted $C_1$ or $C_2$ or $C_3$ or $C_4$ alkylene, and $R^3$ is unsubstituted cycloalkyl. In an exemplary embodiment, $R^2$ is methylene, and $R^3$ is unsubstituted cyclopropyl or unsubstituted cyclobutyl or unsubstituted cyclopentyl or unsubstituted cyclohexyl or unsubstituted cycloheptyl or unsubstituted cyclooctyl.

In an exemplary embodiment, $R^2$ is as described herein, and $R^3$ is unsubstituted cyclohexyl. In an exemplary embodiment, $R^2$ is unsubstituted linear alkylene, and $R^3$ is unsubstituted cyclohexyl. In an exemplary embodiment, $R^2$ is unsubstituted $C_1$ or $C_2$ or $C_3$ or $C_4$ alkylene, and $R^3$ is unsubstituted cyclohexyl. In an exemplary embodiment, $R^2$ is methylene, and $R^3$ is unsubstituted cyclohexyl.

In an exemplary embodiment, $R^2$ is as described herein, and $R^3$ is substituted or unsubstituted heteroaryl. In an exemplary embodiment, $R^2$ is unsubstituted linear alkylene and $R^3$ is substituted or unsubstituted heteroaryl. In an exemplary embodiment, $R^2$ is methylene and $R^3$ is substituted or unsubstituted heteroaryl.

In an exemplary embodiment, the compound has a structure according to the following formula:

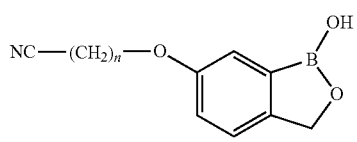

wherein n is 0 or 1 or 2 or 3 or 4 or 5 or 6 or 7 or 8 or 9 or 10, or a salt thereof. In an exemplary embodiment, n is 0. In an exemplary embodiment, n is 1 or 2 or 3 or 4 or 5 or 6 or 7 or 8 or 9 or 10. In an exemplary embodiment, n is 1 or 2 or 3 or 4 or 5. In an exemplary embodiment, n is 1 or 2 or 3. In an exemplary embodiment, n is 2. In an exemplary embodiment, n is 3 or 4 or 5.

In an exemplary embodiment, the compound has a structure according to the following formula:

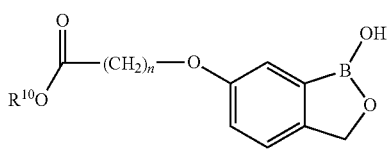

wherein n is 0 or 1 or 2 or 3 or 4 or 5, and $R^{10}$ is $C_1$-$C_6$ alkyl. In an exemplary embodiment, n is as described herein, $R^{10}$ is $C_1$ alkyl. In an exemplary embodiment, n is as described herein, $R^{10}$ is $C_2$ alkyl. In an exemplary embodiment, n is as described herein, $R^{10}$ is $C_3$ alkyl. In an exemplary embodiment, n is as described herein, $R^{10}$ is $C_4$ alkyl. In an exemplary embodiment, n is as described herein, $R^{10}$ is $C_5$ alkyl. In an exemplary embodiment, n is as described herein, $R^{10}$ is $C_6$ alkyl. In an exemplary embodiment, n is 2 and $R^{10}$ is $C_2$ alkyl. In an exemplary embodiment, n is 0 and $R^{10}$ is $C_1$ alkyl. In an exemplary embodiment, n is 0 and $R^{10}$ is as described herein. In an exemplary embodiment, n is 1 and $R^{10}$ is as described herein. In an exemplary embodiment, n is 2 and $R^{10}$ is as described herein. In an exemplary embodiment, n is 2 and $R^{10}$ is $C_1$ alkyl. In an exemplary embodiment, n is 2 and $R^{10}$ is $C_3$ or $C_4$ or $C_5$ or $C_6$ alkyl.

In an exemplary embodiment, the compound has a structure according to the following formula:

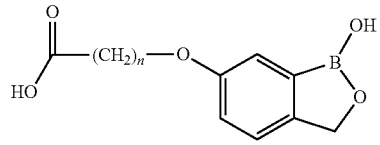

wherein n is 0 or 1 or 2 or 3 or 4 or 5. In an exemplary embodiment, n is 0. In an exemplary embodiment, n is 1. In an exemplary embodiment, n is 2. In an exemplary embodiment, n is 3. In an exemplary embodiment, n is 4. In an exemplary embodiment, n is 5.

In an exemplary embodiment, the compound has a structure according to the following formula:

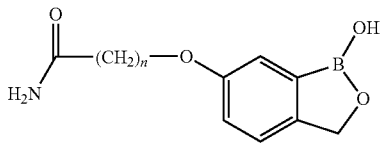

wherein n is 0 or 1 or 2 or 3 or 4 or 5. In an exemplary embodiment, n is 0. In an exemplary embodiment, n is 1. In an exemplary embodiment, n is 2. In an exemplary embodiment, n is 3. In an exemplary embodiment, n is 4. In an exemplary embodiment, n is 5.

In an exemplary embodiment, the compound has a structure according to the following formula:

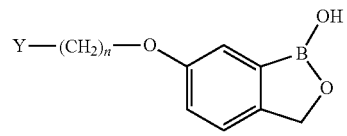

wherein n is 0 or 1 or 2 or 3 or 4 or 5, Y is unsubstituted tetrazolyl, or a salt thereof. In an exemplary embodiment, Y is unsubstituted 1H-tetrazolyl. In an exemplary embodiment, Y is unsubstituted 1H-tetrazol-5-yl. In an exemplary embodiment, Y is as described herein and n is 0. In an exemplary embodiment, Y is as described herein and n is 1 or 2 or 3 or 4 or 5. In an exemplary embodiment, Y is as described herein and n is 1 or 2 or 3. In an exemplary embodiment, Y is as described herein and n is 2. In an exemplary embodiment, Y is as described herein and n is 3 or 4 or 5.

In an exemplary embodiment, the compound has a structure according to the following formula:

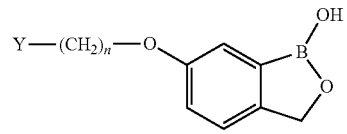

wherein n is 0 or 1 or 2 or 3 or 4 or 5, Y is unsubstituted thiazolidinyl, or a salt thereof. In an exemplary embodiment, n is 0 or 1 or 2 or 3 or 4 or 5, and Y is thiazolidinyl substituted with one or two ketone moieties. In an exemplary embodiment, n is 0 or 1 or 2 or 3 or 4 or 5, and Y is thiazolidinyl 2,4 dione, or a salt thereof. In an exemplary embodiment, Y is as described herein and n is 0. In an exemplary embodiment, Y is as described herein and n is 1 or 2 or 3 or 4 or 5. In an exemplary embodiment, Y is as described herein and n is 1 or 2 or 3. In an exemplary embodiment, Y is as described herein and n is 2. In an exemplary embodiment, Y is as described herein and n is 3 or 4 or 5.

In an exemplary embodiment, the compound has a structure according to the following formula:

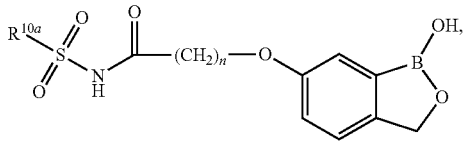

wherein n is 0 or 1 or 2 or 3 or 4 or 5 or 6 and $R^{10a}$ is $C_1$ or $C_2$ or $C_3$ or $C_4$ or $C_5$ or $C_6$ unsubstituted alkyl or $C_3$ or $C_4$ or $C_5$ or $C_6$ unsubstituted cycloalkyl or $NH_2$. In an exemplary embodiment, n is 1 or 2 or 3 or 4 or 5 or 6 and $R^{10a}$ is $C_1$ or $C_2$ or $C_3$ or $C_4$ or $C_5$ or $C_6$ unsubstituted alkyl or $C_3$ or $C_4$ or $C_5$ or $C_6$ unsubstituted cycloalkyl or $NH_2$. In an exemplary embodiment, n is 1 or 2 or 3 and $R^{10a}$ is $C_1$ or $C_2$ or $C_3$ or $C_4$ or $C_5$ or $C_6$ unsubstituted alkyl or $C_3$ or $C_4$ or $C_5$ or $C_6$ unsubstituted cycloalkyl or $NH_2$. In an exemplary embodiment, n is 1 or 2 or 3 and $R^{10a}$ is $C_1$ or $C_2$ or $C_3$ unsubstituted alkyl. In an exemplary embodiment, n is 2 and $R^{10a}$ is $C_1$ unsubstituted alkyl. In an exemplary embodiment, n is 1 or 2 or 3 or 4 or 5 or 6 and $R^{10a}$ is $C_3$ or $C_4$ or $C_5$ or $C_6$ unsubstituted cycloalkyl. In an exemplary embodiment, n is 1 or 2 or 3 and $R^{10a}$ is $C_3$ or $C_4$ or $C_5$ or $C_6$ unsubstituted cycloalkyl. In an exemplary embodiment, n is 2 and $R^{10a}$ is unsubstituted cyclopropyl. In an exemplary embodiment, n is 1 or 2 or 3 or 4 or 5 or 6 and $R^{10a}$ is $NH_2$. In an exemplary embodiment, n is 1 or 2 or 3 and $R^{10a}$ is $NH_2$. In an exemplary embodiment, n is 2 and $R^{10a}$ is $NH_2$.

In an exemplary embodiment, the compound is:

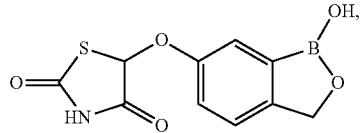 [SMILES: O=C1NC(=O)C(Oc2ccc3c(c2)B(O)OC3)S1]

or a salt thereof.

In an exemplary embodiment, $R^2$ is unsubstituted linear alkylene, and $R^3$ is unsubstituted or halosubstituted thiazolyl. In an exemplary embodiment, $R^2$ is methylene, and $R^3$ is unsubstituted thiazolyl or fluorothiazolyl or chlorothiazolyl. In an exemplary embodiment, the compound has a structure which is:

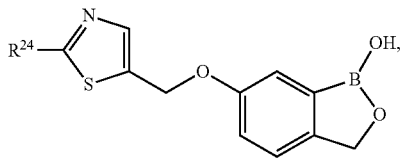

wherein $R^{24}$ is fluoro or chloro. In an exemplary embodiment, the compound is:

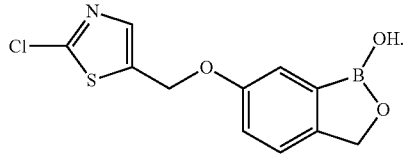 [SMILES: OB1OCc2ccc(OCc3cnc(Cl)s3)cc21]

In an exemplary embodiment, $R^2$ unsubstituted linear alkylene, and $R^3$ is unsubstituted pyridinyl. In an exemplary embodiment, $R^3$ is unsubstituted 4-pyridinyl or 3-pyridinyl or 2-pyridinyl. In an exemplary embodiment, $R^2$ is methylene, and $R^3$ is unsubstituted 4-pyridinyl or 3-pyridinyl or 2-pyridinyl. In an exemplary embodiment, $R^2$ is methylene, and $R^3$ is unsubstituted 2-pyridinyl.

In an exemplary embodiment, $R^2$ unsubstituted linear alkylene, and $R^3$ is unsubstituted or dialkyl isoxazolyl. In an exemplary embodiment, the compound has a structure which is:

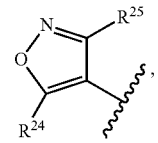

wherein $R^{24}$ and $R^{25}$ are each independently selected unsubstituted alkyl. In an exemplary embodiment, $R^{24}$ and $R^{25}$ are the same. In an exemplary embodiment, $R^{24}$ and $R^{25}$ are different. In an exemplary embodiment, $R^{24}$ and $R^{25}$ are each independently selected unsubstituted $C_1$ or $C_2$ or $C_3$ or $C_4$ or $C_5$ or $C_6$ alkyl. In an exemplary embodiment, $R^2$ is methylene and $R^{24}$ and $R^{25}$ are each methyl.

In an exemplary embodiment, $R^2$ is unsubstituted linear alkylene, and $R^3$ is

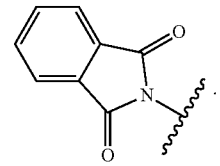 [SMILES: *N1C(=O)c2ccccc2C1=O]

In an exemplary embodiment, $R^2$ is unsubstituted $C_1$ or $C_2$ or $C_3$ or $C_4$ or $C_5$ or $C_6$ alkylene. In an exemplary embodiment, $R^2$ is unsubstituted $C_1$ or $C_2$ or $C_3$ alkylene. In an exemplary embodiment, $R^2$ is propylene.

In an exemplary embodiment, $R^2$ is as described herein, and $R^3$ is $-C(O)NHR^{14}$, wherein $R^{14}$ is selected from the group consisting of H, unsubstituted alkyl and dialkyl substituted aryl. In an exemplary embodiment, $R^2$ is unsubstituted linear alkylene and $R^3$ is $-C(O)NHR^{14}$, wherein $R^{14}$ is selected from the group consisting of H, unsubstituted alkyl and dialkyl substituted aryl. In an exemplary embodiment, $R^2$ is methylene and $R^3$ is $-C(O)NHR^{14}$, wherein $R^{14}$ is selected from the group consisting of H, unsubstituted alkyl and dialkyl substituted aryl. In an exemplary embodiment, $R^{14}$ is H or unsubstituted $C_1$ or $C_2$ or $C_3$ or $C_4$ or $C_5$ or $C_6$ alkyl. In an exemplary embodiment, $R^{14}$ is unsubstituted $C_1$ or $C_2$ or $C_3$ or $C_4$ alkyl. In an exemplary embodiment, $R^2$ is methylene and $R^{14}$ is methyl. In an exemplary embodiment, $R^2$ is methylene and $R^{14}$ is ethyl. In an exemplary embodiment, $R^2$ is methylene and $R^{14}$ is propyl. In an exemplary embodiment, $R^2$ is methylene and $R^{14}$ is tert-butyl. In an exemplary embodiment, $R^{14}$ is unsubstituted dialkylphenyl. In an exemplary embodiment, $R^{14}$ is

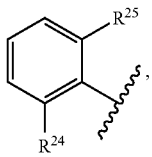

wherein $R^{24}$ and $R^{25}$ are each independently selected unsubstituted alkyl. In an exemplary embodiment, $R^{24}$ and $R^{25}$ are the same. In an exemplary embodiment, $R^{24}$ and $R^{25}$ are different. In an exemplary embodiment, $R^{24}$ and $R^{25}$ are each independently selected unsubstituted $C_1$ or $C_2$ or $C_3$ or $C_4$ or $C_5$ or $C_6$ alkyl. In an exemplary embodiment, $R^2$ is methylene and $R^{24}$ and $R^{25}$ are each methyl.

In an exemplary embodiment, the compound is:

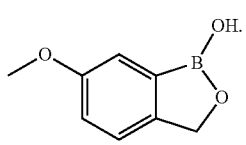

In an exemplary embodiment, the compound is:

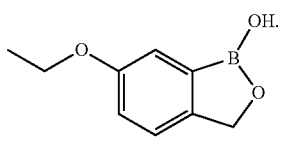

In an exemplary embodiment, the compound is:

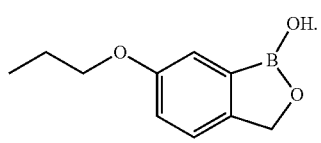

In an exemplary embodiment, the compound is:

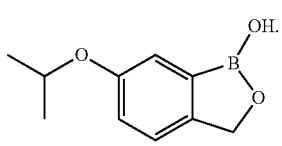

In an exemplary embodiment, the compound is:

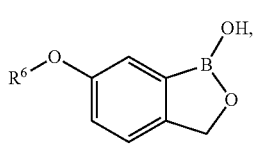

wherein $R^6$ is $C_4$ unsubstituted alkyl. In an exemplary embodiment, the compound is:

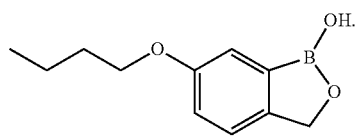

In an exemplary embodiment, the compound is:

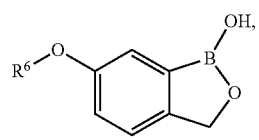

wherein $R^6$ is $C_5$ unsubstituted alkyl. In an exemplary embodiment, the compound is:

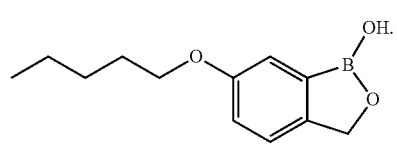 [SMILES: CCCCCOc1ccc2c(c1)B(O)OC2]

In an exemplary embodiment, the compound is:

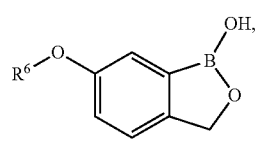

wherein $R^6$ is $C_6$ unsubstituted alkyl. In an exemplary embodiment, the compound is:

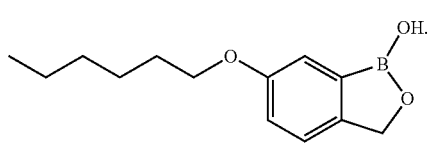 [SMILES: CCCCCCOc1ccc2c(c1)B(O)OC2]

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In an exemplary embodiment, alkyl is branched alkyl. In another exemplary embodiment, heteroalkyl is linear heteroalkyl. In another exemplary embodiment, heteroalkyl is branched heteroalkyl.

III.b) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is berenil. In an exemplary embodiment, the additional therapeutic agent is diminazene. In an exemplary embodiment, the additional therapeutic agent is an antiprotozoa. In an exemplary embodiment, the additional therapeutic agent is selected from the group consisting of benznidazole, buparvaquone, carbarsone, clioquinol, disulfuram, eflornithine, emetine, etofamide, furazolidone, meglumine antimoniate, melarsoprol, metronidazole, miltefosine, nifurtimox, nimorazole, nitazoxanide, ornidazole, paromomycin sulfate, pentamidine, pyrimethamine, secnidazole and timidazole. In an exemplary embodiment, the additional therapeutic agent is pentamidine. In an exemplary embodiment, the additional therapeutic agent is suramin. In an exemplary embodiment, the additional therapeutic agent is eflornithine. In an exemplary embodiment, the additional therapeutic agent is melarsoprol. In an exemplary embodiment, the additional therapeutic agent is nifurtimox. In an exemplary embodiment, the additional therapeutic agent is benznidazole. In an exemplary embodiment, the additional therapeutic agent contains a 5-nitrofuran moiety. In an exemplary embodiment, the additional therapeutic agent contains a 5-nitroimidazolyl moiety. In an exemplary embodiment, the additional therapeutic agent is fexinidazole. In an exemplary embodiment, the additional therapeutic agent is an antiparasitic. In an exemplary embodiment, the additional therapeutic agent is selected from the group consisting of amitraz, avermectin, carbadox, diethylcarbamazine, dimetridazole, diminazene, ivermectin, macrofilaricide, malathion, mitaban, organophosphate, oxamniquine, permethrin, praziquantel, pyrantel pamoate, selamectin, sodium stibogluconate and thiabendazole. In an exemplary embodiment, the additional therapeutic agent is selected from the group consisting of antimony, meglumine antimoniate, sodium stibogluconate, amphotericin, miltefosine and paromomycin.

In an exemplary embodiment, the additional therapeutic agent is an antimalarial. In an exemplary embodiment, the additional therapeutic agent is artemisinin. In an exemplary embodiment, the additional therapeutic agent is an artemisinin derivative. In an exemplary embodiment, the additional therapeutic agent is an artemisinin derivative which is artesunate or artemether or artemotil or dihydroartemisinin. In an exemplary embodiment, the additional therapeutic agent is selected from the group consisting of lumefantrine, artemether-lumefantrine, amodiaquine, artesunate-amodiaquine, artesunate-mefloquine, artesunate-sulfadoxine/pyrimethamine, atovaquone-proguanil, quinine, chloroquine, cotrifazid, doxycycline, mefloquine, primaquine, proguanil, sulfadoxine-pyrimethamine, hydroxychloroquine, sulfalene-pyrimethamine, dapsone, proguanil-dapsone and chloroproguanil-dapsone. In an exemplary embodiment, the additional therapeutic agent is selected from the group consisting of amodiaquine, chloroquine and sulfadoxine-pyrimethamine. In an exemplary embodiment, the additional therapeutic agent is mefloquine. In an exemplary embodiment, the additional therapeutic agent is selected from the group consisting of halofantrine, dihydroartemisinin-piperaquine, piperaquine, pyronaridine and tetracycline.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRO®-A; Schering-Plough), interferon alfacon-1 (INFERGEN®; Intermune), peginterferon alpha-2b (PEGINTRONT™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

III.c) Preparation of Boron-Containing Compounds

Compounds of use in the invention can be prepared using commercially available starting materials, known intermediates, or by using the synthetic methods described herein, or published in references described and incorporated by reference herein, such as PCT Pub. No. WO2008157726 and U.S. Pat. Pubs. US20060234981, US20070155699 and US20070293457.

To make 6-O substituted compounds such as C ($R^2$ and $R^3$ as defined herein), phenol H181 can be reacted with corresponding halide B under basic conditions such as sodium hydride or potassium carbonate.

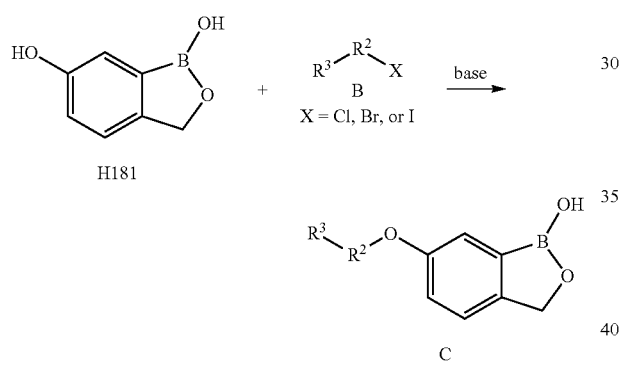

Compounds such as E can be prepared by reacting phenol H181 with the corresponding halide D (X=Cl, Br, I; n=1, 2, 3 . . . ) under basic conditions such as sodium hydride or potassium carbonate.

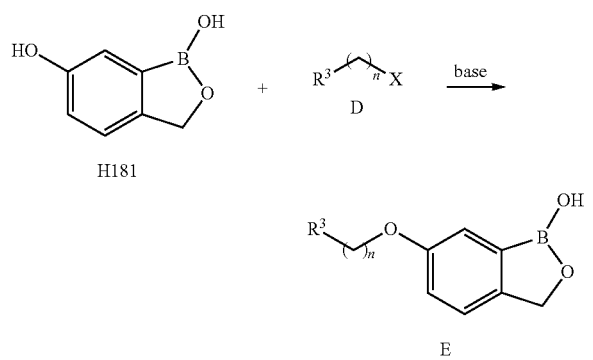

Esters such as G can be prepared by reacting phenol H181 with corresponding α-bromoacetates such as F under basic conditions such as sodium hydride.

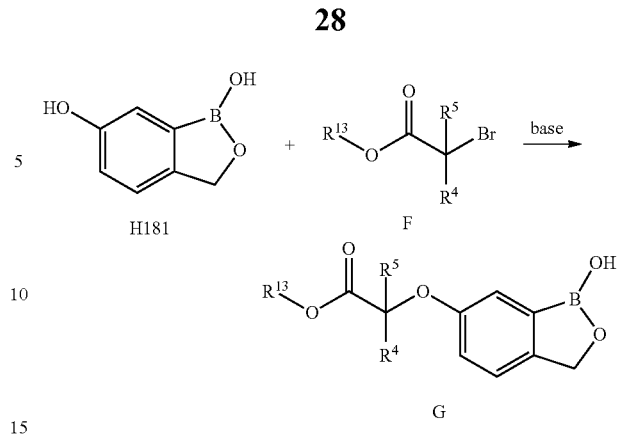

Ketones such as compound I can be prepared by reacting phenol H181 with corresponding α-bromoketones such as H under basic conditions such as sodium hydride.

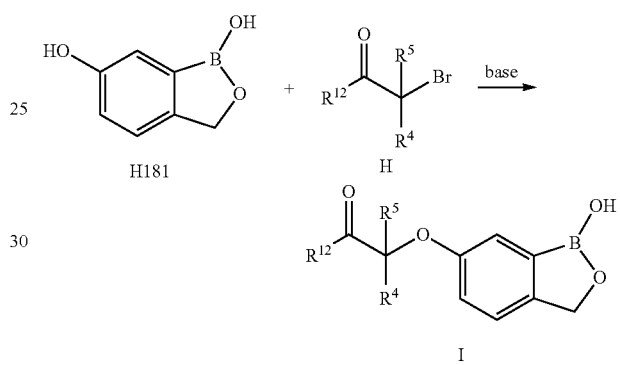

To synthesize a compound with linker that is longer than methylene (for example, ethylene or propylene), the reaction condition would be the same as synthesis of methylene linker. For example, to synthesize a compound where $R^2$ is a propylene moiety, the following scheme can be utilized:

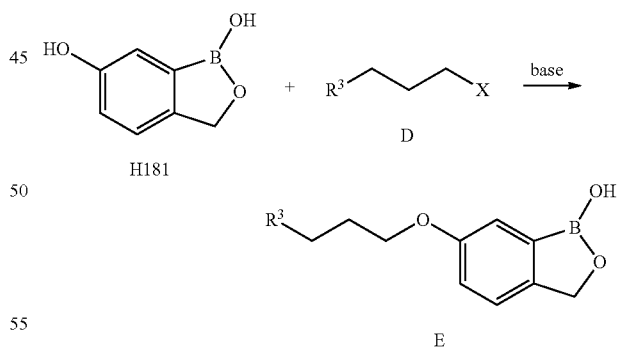

The compounds of the invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T evansi, T. hosei, T. levisi, T. melophagium, T. parroti, T percae, T rangeli, T. rotatorium, T. rugosae, T. sergenti, T. simiae, T sinipercae, T. suis, T. theileri, T. triglae* and *T. vivax*. In another exemplary embodiment, the protozoa is a *Trypanosoma brucei*. In another exemplary embodiment, the protozoa is *Trypanosoma brucei brucei*. In another exemplary embodiment, the protozoa is *Trypanosoma brucei rhodesiense*. In another exemplary embodiment, the protozoa is *Trypanosoma brucei gambiense*. In another exemplary embodiment, the protozoa is *Trypanosoma cruzi*. In another exemplary embodiment, the protozoa is *Trypanosoma cruzi* in the trypomastigote form. In another exemplary embodiment, the protozoa is *Trypanosoma cruzi* in the amastigote form. In another exemplary embodiment, the protozoa is *Trypanosoma cruzi* in the epimastigote form. In another exemplary embodiment, the protozoa is transmitted to the animal described herein by a triatomine bug infected with the protozoa. In another exemplary embodiment, the protozoa is transmitted to the animal described herein by a reduvid bug infected with the protozoa. In another exemplary embodiment, the protozoa is transmitted to the animal described herein by a rhodnius prolixus infected with the protozoa. In another exemplary embodiment, the protozoa is a member of the genus *Leishmania*. In another exemplary embodiment, the protozoa is a member of *Leishmania Viannia*. In an exemplary embodiment, the protozoa is selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the protozoa is *L. donovani*. In an exemplary embodiment, the protozoa is *L. infantum*. In another exemplary embodiment, the protozoa is a member of the genus *Plasmodium*. In another exemplary embodiment, the protozoa is selected from the group consisting of *Plasmodium falciparum, Plasmodium vivax, Plasmodium ovale, Plasmodium vivax, Plasmodium malariae* and *Plasmodium knowlesi*. In another exemplary embodiment, the protozoa is selected from the group consisting of *Plasmodium vivax, Plasmodium ovale, Plasmodium vivax* and *Plasmodium malariae*. In another exemplary embodiment, the protozoa is *Plasmodium falciparum*. In another exemplary embodiment, the protozoa is transmitted to the animal described herein by a mosquito infected with the protozoa. In another exemplary embodiment, wherein the protozoa is transmitted to the animal described herein by an *Anopheles* mosquito containing the protozoa. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Methods of Treating and/or Preventing Disease

The compounds of the invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the animal is not otherwise is need of treatment with the compound of the invention. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is selected from the group consisting of *T. avium, T. boissoni, T. brucei, T carassii, T cruzi, T. congolense, T. equinum, T. equiperdum, T evansi, T. hosei, T levisi, T. melophagium, T. parroti, T percae, T. rangeli, T rotatorium, T. rugosae, T. sergenti, T. simiae, T sinipercae, T suis, T. theileri, T triglae* and *T. vivax*. In an exemplary embodiment, the disease is associated with a *Trypanosoma brucei*. In an exemplary embodiment, the disease is associated with *Trypanosoma brucei brucei*. In an exemplary embodiment, the disease is associated with *Trypanosoma brucei rhodesiense*. In an exemplary embodiment, the disease is associated with *Trypanosoma brucei gambiense*. In an exemplary embodiment, the disease is associated with *Trypanosoma cruzi*. In an exemplary embodiment, the disease is a typanosomiasis. In an exemplary embodiment, the disease is a human typanosomiasis. In an exemplary embodiment, the disease is an animal typanosomiasis. In an exemplary embodiment, the disease is selected from the group consisting of nagana, surra, mal de caderas, murrina de caderas, dourine, cachexial fevers, Gambian horse sickness, baleri, kaodzera, tahaga, galziekte or galzietzke and pesteboba. In an exemplary embodiment, the disease is selected from the group consisting of Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is acute phase Chagas disease. In an exemplary embodiment, the disease is chronic phase Chagas disease. In an exemplary embodiment, the disease is the indeterminate form of chronic phase Chagas disease. In an exemplary embodiment, the disease is the determinate form of chronic phase Chagas disease. In an exemplary embodiment, the disease is chronic Chagasic cardiomyopathy. In an exemplary embodiment, the disease is chronic Chagasic cardiomyopathy with concomitant megaviscera. In an exemplary embodiment, the disease is chronic Chagasic cardiomyopathy with concomitant megaesophagus. In an exemplary embodiment, the disease is chronic Chagasic cardiomyopathy with concomitant megacolon. In an exemplary embodiment, the disease is dysphagia. In an exemplary embodiment, the disease is sleeping sickness (or African sleeping sickness). In an exemplary embodiment, the disease is acute phase sleeping sickness. In an exemplary embodiment, the disease is chronic phase sleeping sickness. In an exemplary embodiment, the disease is an acute phase of a typanosomiasis. In an exemplary embodiment, the disease is a chronic phase of a typanosomiasis. In an exemplary embodiment, the disease is the non-CNS form of a typanosomiasis. In an exemplary embodiment, the disease is the CNS form of a typanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania Viannia*. In an exemplary embodiment, the disease is associated with a member selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis,* and *L. (V.) peruviana*. In an exemplary embodiment, the disease is associated with *L. donovani*. In an exemplary embodiment, the disease is associated with *L. infantum*. In an exemplary embodiment, the disease is leishmaniasis. In an exemplary embodiment, the disease is a member selected from visceral leishmaniasis and/or cutaneous leishmaniasis. In an exemplary embodiment, the disease is diffuse cutaneous leishmaniasis and/or mucocutaneous leishmaniasis. In another exemplary embodiment, the disease is associated with a member of the genus *Plasmodium*. In another exemplary embodiment, the disease is associated with a member selected from the group consisting of *Plasmodium falciparum, Plasmodium vivax, Plasmodium ovale, Plasmodium vivax, Plasmodium malariae* and *Plasmodium knowlesi*. In another exemplary embodiment, the disease is associated with a member selected from the group consisting of *Plasmodium vivax, Plasmodium ovale, Plasmodium vivax* and *Plasmodium malariae*. In another exemplary embodiment, the disease is associated with *Plasmodium falciparum*. In another exemplary embodiment, the disease is transmitted to the animal described herein by a mosquito infected with the protozoa. In another exemplary embodiment, the disease is transmitted to the animal described herein by an *Anopheles* mosquito containing the protozoa. In another exemplary embodiment, the disease is malaria. In another exemplary embodiment, the disease is cerebral malaria. In another exemplary embodiment, the disease is chronic malaria. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a)

a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure which is

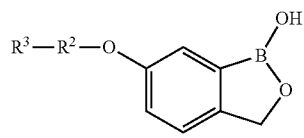

or a salt, hydrate, or solvate thereof, wherein $R^2$ is selected from the group consisting of unsubstituted linear alkylene, alkylene substituted with unsubstituted alkyl, alkylene substituted with unsubstituted aryl; $R^3$ is selected from the group consisting of unsubstituted linear alkylene, alkylene substituted with unsubstituted alkyl, alkylene substituted with unsubstituted aryl, and $R^3$ is selected from the group consisting of halosubstituted alkyl, unsubstituted cycloalkyl, halosubstituted or unsubstituted heteroaryl, vinyl, hydroxy substituted alkyl, —C(O)H, —C(O)R$^{12}$, —C(O)OR$^{13}$, C(O)NHR$^{14}$, —OR$^{10}$ and —NHR$^{11}$ wherein $R^{10}$ is selected from the group consisting of H, unsubstituted alkyl, unsubstituted heterocycloalkyl; $R^{11}$ is selected from the group consisting of C(O)OR$^{20}$, wherein $R^{20}$ is unsubstituted alkyl $R^{12}$ is unsubstituted alkyl; $R^{13}$ is selected from the group consisting of H, unsubstituted alkyl, unsubstituted alkoxy methyl; $R^{14}$ is selected from the group consisting of H, unsubstituted alkyl, unsubstitutedalkyl substituted aryl.

In an exemplary embodiment, according to the above paragraph, having a structure according to the following formula:

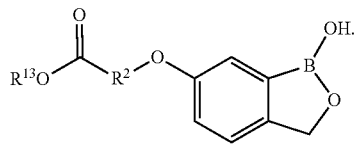

In an exemplary embodiment, the invention provides a combination comprising the compound according to any of the above paragraphs, together with at least one other therapeutically active agent.

In an exemplary embodiment, the invention provides a pharmaceutical composition comprising the compound according to any of the above paragraphs, and a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with an effective amount of the compound according to any of the above paragraphs, thereby killing and/or preventing the growth of the protozoa.

In an exemplary embodiment, according to any of the above paragraphs, the protozoa is a member of the *trypanosoma* genus.

In an exemplary embodiment, according to any of the above paragraphs, the protozoa is *Trypanosoma*.

In an exemplary embodiment, according to any of the above paragraphs, the protozoa is *Trypanosoma brucei*.

In an exemplary embodiment, according to any of the above paragraphs, the *Trypanosoma brucei* is a member selected from *Trypanosoma brucei brucei*, *Trypanosoma brucei gambiense* and *Trypanosoma brucei rhodesiense*.

In an exemplary embodiment, the invention provides a method of treating and/or preventing a disease in an animal, comprising: administering to the animal a therapeutically effective amount of the compound according to any of the above paragraphs, thereby treating and/or preventing the disease.

In an exemplary embodiment, according to any of the above paragraphs, the disease is African sleeping sickness.

In an exemplary embodiment, according to any of the above paragraphs, the animal is a human.

In an exemplary embodiment, according to any of the above paragraphs, the invention is a use of a compound of the invention or a combination of the invention in the manufacture of a medicament for the treatment and/or prophylaxis of protozoal infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepackaged silica gel), which were run with a maximum capacity of 1 g crude sample per 10 g silica gel. Samples were preloaded on Celite in Analogix Sample Loading Cartridges with fits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 $C_{18}$ column, Dyonex Chromeleon operating system coupled with a Varian Prostar 320 UV-vis detector (254 nm) and a Sedex55 ELS detector. Conditions: Solvent A: $H_2O$/1% acetonitrile/0.1% $HCO_2H$; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

All solvents used were commercially available and were used without further purification. Reactions were typically run using anhydrous solvents under an inert atmosphere of $N_2$.

Compounds are named using the AutoNom 2000 add-on for MDL ISIS™ Draw 2.5 SP2 or their catalogue name if commercially available.

Starting materials used were either available from commercial sources or prepared according to literature procedures and had experimental data in accordance with those reported. 6-aminobenzo[c][1,2]oxaborol-1(3H)-ol (C50), for example, can be synthesized according to the methods described in U.S. Pat. Pubs. US20060234981 and US20070155699.

Example 1

6-Benzyloxy-1,3-dihydro-1-hydroxy-2,1-benzoxaborole (H178)

[3-Benzyloxy-6-(((tetrahydro-2H-pyran-2-yl)oxy)methyl)]bromobenzene (40)

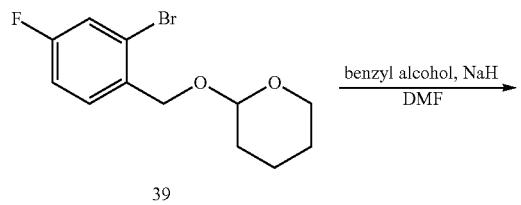

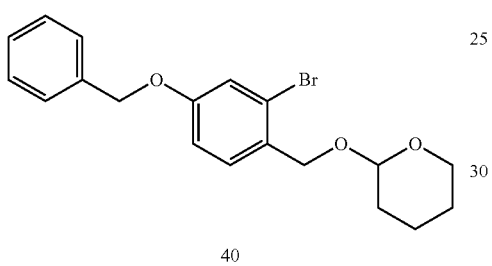

Compound 39 (1 mmol) was dissolved in DMF (20 mL) and cooled to 0° C. with ice bath. To this solution under nitrogen were added in sequence sodium hydride (353 mg, 8.8 mmol, 2.5 eq) and benzyl alcohol (0.76 g, 7.06 mmol, 2.0 eq). The reaction mixture was stirred for 1 hour at 100° C. then treated with cold water (30 ml). After extraction with ethyl acetate, the organic layer was washed with water and brine. The residue after rotary evaporation was purified by column chromatography over silica gel to give compound 40 (0.86 g, 64.8% yield). $^1$H NMR (300 MHz, CDCl$_3$): δ 7.39 (m, 6H), 7.20 (dd, J=3.2 Hz, 1H), 6.92 (dd, J=11.2 & 3.2 Hz, 1H), 5.04 (s, 2H), 4.79 (s, 0.5H), 4.75 (s, 1.5H), 4.52 (s, 1H), 3.93 (m, 1H), 3.55 (m, 1H) and 1.70 (m, 6H) ppm.

6-Benzyloxy-1,3-dihydro-1-hydroxy-2,1-benzoxaborole (H178)

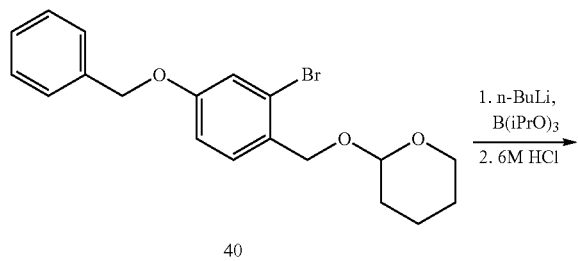

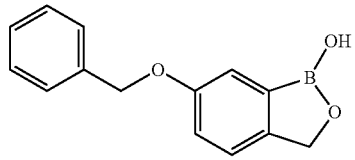

Compound 40 (0.86 g, 2.28 mmol) was dissolved in anhydrous THF (200 mL) and cooled to −80° C. To this solution under nitrogen was added dropwise 1.6M n-BuLi (1.64 mL, 2.62 mmol, 1.15 eq) over 20 minutes. After the mixture was stirred for another 20 minutes at −80° C., B(iPrO)$_3$ (0.61 mL, 2.62 mmol, 1.15 eq) was added dropwise over 8 minutes. The mixture was allowed to warm to room temperature gradually and stirred overnight at room temperature. After 6M HCl (6 mL) was added and stirred for 2 hours, the mixture was evaporated and extracted with ethyl acetate (25 mL×5) and dried over anhydrous Na$_2$SO$_4$. The residue after rotary evaporation was purified by crystallization to give the title compound (0.36 g, 66% yield). $^1$H NMR (300 MHz, DMSO-d$_6$): δ 9.12 (s, 1H), 7.38 (m, 7H), 7.11 (dd, J=7.2 & 3.2 Hz, 1H), 5.10 (s, 2H) and 4.90 (s, 2H) ppm. Mp 118-119° C.

6-Cyclohexylmethoxy-1,3-dihydro-1-hydroxy-2,1-benzoxaborole (H179)

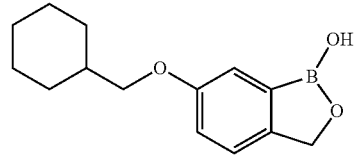 [SMILES: OB1OCc2ccc(OCC3CCCCC3)cc21]

H181 (0.667 mmol) was dissolved in DMF (10 mL) and cooled to 0° C. with ice bath. To this solution under nitrogen were added in sequence sodium hydride (106 mg, 2.67 mmol, 4.0 eq) and (bromomethyl)cyclohexane (0.372 ml, 2.67 mmol, 4.0 eq). The reaction mixture was stirred for 18 hours then treated with 1M HCl (10 ml). After extraction with ethyl acetate, the organic layer was washed with water and brine, and dried over anhydrous Na$_2$SO$_4$. The residue after rotary evaporation was purified by column chromatography over silica gel to give the title compound (109.2 mg, 66% yield). $^1$H NMR (300 MHz, DMSO-d$_6$): δ 9.08 (s, 1H), 7.29 (d, J=8.4 Hz, 1H), 7.23 (d, J=2.4 Hz, 1H), 7.03 (dd, J=8.4 & 2.7 Hz, 1H), 4.90 (m, 2H), 3.78 (d, J=6.3 Hz, 2H) and 1.83-1.01 (m, 11H) ppm. Mp 126-127° C.

6-(Pyridin-2-ylmethoxy)-1,3-dihydro-1-hydroxy-2,1-benzoxaborole (H180)

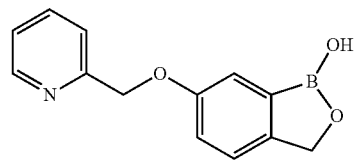 [SMILES: OB1OCc2ccc(OCc3ccccn3)cc21]

The title compound was synthesized using the same condition as that of H188. $^1$H NMR (300 MHz, DMSO-d$_6$): δ 9.14 (s, 1H), 8.59-8.56 (m, 2H), 7.46-7.42 (m, 2H), 7.33 (d, J=8.4 Hz, 1H), 7.29 (d, J=2.4 Hz, 1H), 7.15 (dd, J=8.4 & 2.4 Hz, 1H), 5.21 (s, 2H) and 4.92 (s, 2H) ppm. Mp 167-170° C.

6-Hydroxyl-1,3-dihydro-1-hydroxy-2,1-benzoxaborole (H181)

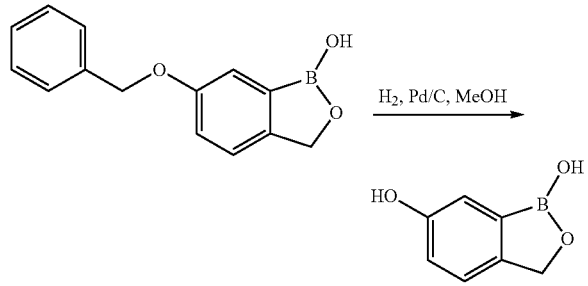

H178 (13 mmol) was dissolved in MeOH (300 mL). To this solution under nitrogen was added 10% Pd/C (200 mg). The reaction mixture was vacuumed and backfilled hydrogen for 3 times, then stirred overnight at room temperature. After filtration and rotary evaporation, the residue was purified by recrystallization to give H181 (1.98 mg, 98% yield). $^1$H NMR (300 MHz, DMSO-$d_6$): δ 9.29 (s, 1H), 9.04 (s, 1H), 7.18 (d, J=8.4 Hz, 2H), 6.87 (dd, J=8.1 & 2.4 Hz, 1H) and 4.86 (s, 2H) ppm. Mp 133-135° C.

6-Methoxy-1,3-dihydro-1-hydroxy-2,1-benzoxaborole (H182)

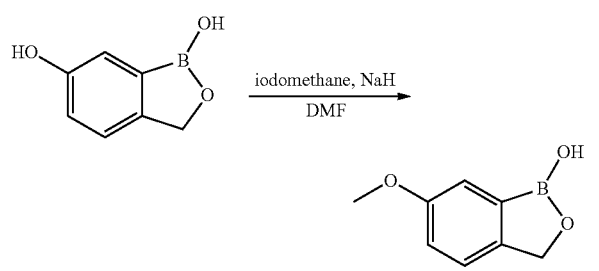

H181 (150 mg, 1.0 mmol) was dissolved in DMF (8.0 mL) and cooled to 0° C. with ice bath. To this solution under nitrogen were added in sequence NaH (60% in mineral oil, 120 mg, 3.0 mmol) and iodomethane (0.1 mL, 2.0 mmol). The reaction mixture was stirred for 2 h then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (81.9 mg, 50% yield). $^1$H NMR (400 MHz, CDCl$_3$): δ 7.26 (d, J=8.4 Hz, 1H), 7.23 (d, J=2.4 Hz, 1H), 7.07 (dd, J=8.1 & 2.4 Hz, 1H), 5.06 (s, 2H) and 3.84 (s, 3H) ppm; Mp: 107-109° C.

6-Ethoxy-1,3-dihydro-1-hydroxy-2,1-benzoxaborole (H183)

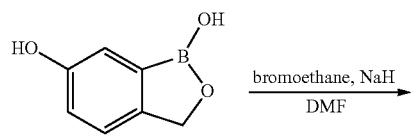

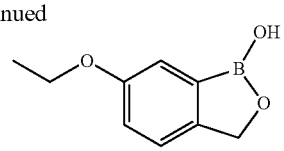

H181 (110 mg, 0.73 mmol) was dissolved in DMF (6.0 mL) and cooled to 0° C. with ice bath. To this solution under nitrogen were added in sequence NaH (60% in mineral oil, 117 mg, 2.93 mmol) and bromoethane (0.22 mL, 2.93 mmol). The reaction mixture was stirred for 1 d then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (85 mg, 65% yield). $^1$H NMR (300 MHz, DMSO-$d_6$): δ 9.13 (s, 1H), 7.29 (d, J=8.1 Hz, 1H), 7.20 (d, J=2.4 Hz, 1H), 7.03 (dd, J=8.1 & 2.4 Hz, 1H), 4.91 (s, 2H), 4.02 (q, J=7.0 Hz, 2H) and 1.33 (t, J=7.2 Hz, 3H) ppm; Mp: 80-82° C.

6-Propoxy-1,3-dihydro-1-hydroxy-2,1-benzoxaborole (H184)

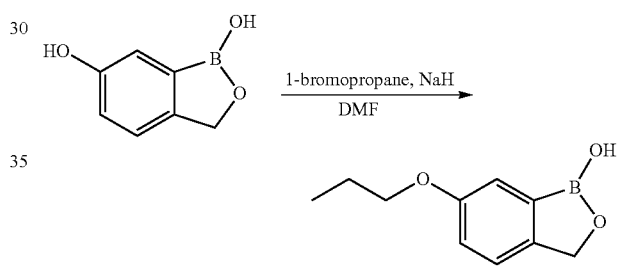

H181 (110 mg, 0.73 mmol) was dissolved in DMF (6.0 mL) and cooled to 0° C. with ice bath. To this solution under nitrogen were added in sequence NaH (60% in mineral oil, 117 mg, 2.93 mmol) and 1-bromopropane (0.26 mL, 2.93 mmol). The reaction mixture was stirred for 1 d then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (89 mg, 64% yield). $^1$H NMR (400 MHz, DMSO-$d_6$): δ 9.10 (s, 1H), 7.29 (d, J=8.4 Hz, 1H), 7.23 (d, J=2.4 Hz, 1H), 7.03 (dd, J=8.1 & 2.4 Hz, 1H), 4.91 (s, 2H), 3.92 (t, J=6.8 Hz, 2H), 1.78-1.68 (m, 2H) and 0.98 (t, J=7.2 Hz, 3H) ppm; Mp: 80-81° C.

6-Isopropoxy-1,3-dihydro-1-hydroxy-2,1-benzoxaborole (H185)

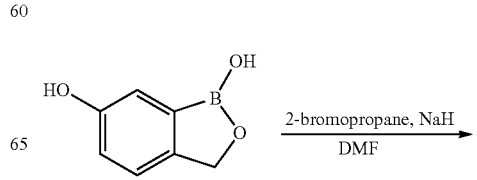

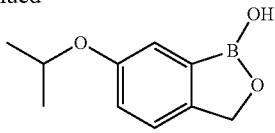

H181 (150 mg, 1.0 mmol) was dissolved in DMF (8.0 mL) and cooled to 0° C. with ice bath. To this solution under nitrogen were added in sequence NaH (60% in mineral oil, 160 mg, 4.0 mmol) and 2-bromopropane (0.40 mL, 4.0 mmol). The reaction mixture was stirred for 2 d then treated with 1.0 M HCl (10.0 mL). After extraction with ethyl acetate, the organic phase was washed with water and brine, and dried over anhydrous Na$_2$SO$_4$. The residue after rotary evaporation was purified by column chromatography over silica gel to give the title compound (118 mg, 61.5% yield). $^1$H NMR (300 MHz, DMSO-d$_6$): δ 9.10 (s, 1H), 7.27 (d, J=8.4 Hz, 1H), 7.23 (d, J=2.4 Hz, 1H), 7.01 (dd, J=8.1 & 2.4 Hz, 1H), 4.90 (s, 2H), 4.63-4.53 (m, 1H) and 1.27 (d, J=6 Hz, 6H) ppm; Mp: 62-65° C.

6-Allyloxy-1,3-dihydro-1-hydroxy-2,1-benzoxaborole (H186)

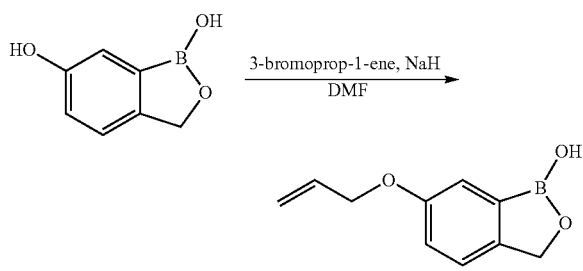

H181 (200 mg, 1.33 mmol) was dissolved in DMF (8.0 mL) and cooled to 0° C. with ice bath. To this solution under nitrogen were added in sequence NaH (60% in mineral oil, 213 mg, 5.33 mmol) and 3-bromoprop-1-ene (0.46 mL, 5.33 mmol). The reaction mixture was stirred for 5 h then treated with 1.0 M HCl (10.0 mL). After extraction with ethyl acetate, the organic phase was washed with water and brine, and dried over anhydrous Na$_2$SO$_4$. The residue after rotary evaporation was purified by column chromatography over silica gel to give the title compound (160.5 mg, 63.5% yield). $^1$H NMR (400 MHz, CDCl$_3$): δ 7.25 (d, J=8.4 Hz, 1H), 7.23 (d, J=2.4 Hz, 1H), 7.09 (dd, J=8.1 & 2.4 Hz, 1H), 6.12-6.02 (m, 1H), 5.42 (dd, J=17.2 & 1.6 Hz, 1H), 5.29 (dd, J=17.2 & 1.6 Hz, 1H), 5.06 (s, 2H) and 4.57 (d, J=2.8 Hz, 2H) ppm; Mp: 79-81° C.

6-Butyloxy-1,3-dihydro-1-hydroxy-2,1-benzoxaborole (H187)

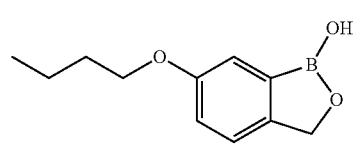

H181 (1 mmol) was dissolved in DMF (10 mL) and cooled to 0° C. with ice bath. To this solution under nitrogen were added in sequence sodium hydride (160 mg, 4 mmol, 4.0 eq) and 1-chlorobutane (0.424 mL, 4 mmol, 4.0 eq). The reaction mixture was stirred for 2 days then treated with 1M HCl (10 ml). After extraction with ethyl acetate, the organic layer was washed with water and brine, and dried over anhydrous Na$_2$SO$_4$. The residue after rotary evaporation was purified by column chromatography over silica gel to give the title compound (45.7 mg, 22% yield). $^1$H NMR (300 MHz, DMSO-d$_6$): δ 9.09 (s, 1H), 7.29 (d, J=8.4 Hz, 1H), 7.23 (d, J=2.4 Hz, 1H), 7.03 (dd, J=8.1 & 2.4 Hz, 1H), 4.91 (s, 2H), 3.90 (t, J=6.6 Hz, 2H), 1.70 (m, 2H), 1.44 (m, 2H) and 0.936 (t, J=7.5 Hz, 3H) ppm. Mp 92-94° C.

6-((2'-Chloro)thiazol-5-yl)methoxy-1,3-dihydro-1-hydroxy-2,1-benzoxaborole (H188)

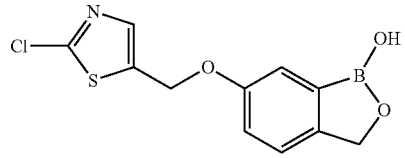 [SMILES: OB1OCc2ccc(OCc3cnc(Cl)s3)cc21]

H181 (0.667 mmol) was dissolved in DMF (10 mL) and cooled to 0° C. with ice bath. To this solution under nitrogen were added in sequence sodium hydride (106 mg, 2.67 mmol, 4.0 eq) and 2-chloro-5-(chloromethyl)thiazole (0.298 mL, 2.67 mmol, 4.0 eq). The reaction mixture was stirred for 4 hours then treated with 1M HCl (10 ml). After extraction with ethyl acetate, the organic layer was washed with water and brine, and dried over anhydrous Na$_2$SO$_4$. The residue after rotary evaporation was purified by column chromatography over silica gel to give the title compound (66 mg, 35% yield). $^1$H NMR (400 MHz, DMSO-d$_6$): δ 9.16 (s, 1H), 7.92 (d, J=4 Hz, 1H), 7.34 (d, J=8.8 Hz, 2H), 7.13 (dd, J=8.0 & 2.7 Hz, 1H), 5.35 (s, 2H) and 4.92 (s, 2H) ppm. Mp 112-114° C.

6-((3,5-Dimethylisoxazol-4-yl)methoxy)-1,3-dihydro-1-hydroxy-2,1-benzoxaborole (H189)

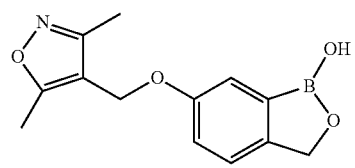 [SMILES: Cc1noc(C)c1COc1ccc2c(c1)B(O)OC2]

The title compound was synthesized using the same condition as that of H188. $^1$H NMR (300 MHz, DMSO-d$_6$): δ 9.14 (s, 1H), 7.35-7.31 (m, 2H), 7.12 (dd, J=8.1 & 2.4 Hz, 1H), 4.92 (s, 4H), 2.40 (s, 3H) and 2.12 (s, 3H) ppm. Mp 129-131° C.

Methyl[2-(1,3-dihydro-1-hydroxy-2,1-benzoxaborol-6-yloxy)]acetamide (H190)

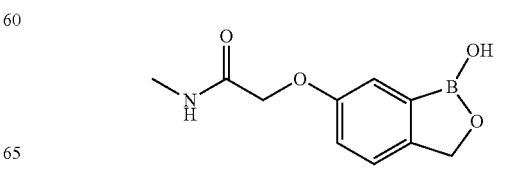

The title compound was synthesized using the same condition as that of H193. ¹H NMR (300 MHz, DMSO-d₆): δ 9.17 (s, 1H), 8.02 (s, 1H), 7.33 (d, J=8.4 Hz, 1H), 7.24 (d, J=2.4 Hz, 1H), 7.10 (dd, J=8.4 & 2.7 Hz, 1H), 4.92 (s, 2H), 4.46 (s, 2H) and 2.65 (d, J=4.8 Hz, 3H) ppm. Mp 159-161° C.

Ethyl[2-(1,3-dihydro-1-hydroxy-2,1-benzoxaborol-6-yloxy)]acetamide (H191)

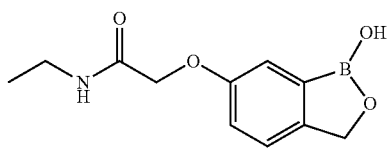 [SMILES: CCNC(=O)COc1ccc2c(c1)B(O)OC2]

The title compound was synthesized using the same condition as that of H193. ¹H NMR (400 MHz, DMSO-d₆): δ 9.17 (s, 1H), 8.09 (t, J=6 Hz, 1H), 7.33 (d, J=8.4 Hz, 1H), 7.24 (d, J=2.4 Hz, 1H), 7.10 (dd, J=8.4 & 2.7 Hz, 1H), 4.92 (s, 2H), 4.45 (s, 2H), 3.19-3.11 (m, 2H) and 3.04 (t, J=7.2 Hz, 3H) ppm. Mp 118° C.-119° C.

N-propyl-2-(1,3-dihydro-1-hydroxy-2,1-benzoxaborol-6-yloxy)acetamide (H192)

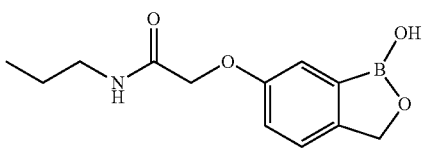 [SMILES: CCCNC(=O)COc1ccc2c(c1)B(O)OC2]

H181 (0.667 mmol) was dissolved in DMSO (10 mL). To this solution under nitrogen were added potassium carbonate (368 mg, 2.67 mmol, 4.0 eq), a catalytic amount of NaI and 2-chloro-N-propylacetamide (360 mg, 2.67 mmol, 4.0 eq). The reaction mixture was stirred for 15 hours at 90° C. then treated with 1M HCl (10 ml). After extraction with ethyl acetate, the organic layer was washed with water and brine, and dried over anhydrous Na₂SO₄. The residue after rotary evaporation was purified by column chromatography over silica gel and recrystallization to give the title compound (60 mg, 36% yield). ¹H NMR (400 MHz, DMSO-d₆): δ 9.15 (s, 1H), 8.06 (s, 1H), 7.32 (d, J=8.1 Hz, 1H), 7.24 (d, J=2.4 Hz, 1H), 7.09 (dd, J=8.4 & 2.7 Hz, 1H), 4.92 (s, 2H), 4.63 (s, 2H), 3.09 (q, J=6.6 Hz, 2H), 1.43 (m, J=6.9 Hz, 2H) and 0.81 (t, J=7.2 Hz, 3H) ppm. Mp 136-138° C.

N-tert-butyl-2-(1,3-dihydro-1-hydroxy-2,1-benzoxaborol-6-yloxy)acetamide (H193)

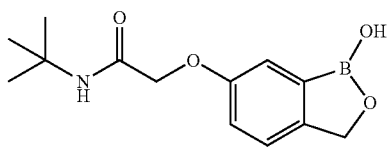 [SMILES: CC(C)(C)NC(=O)COc1ccc2c(c1)B(O)OC2]

H181 (0.333 mmol) was dissolved in DMSO (5 mL). To this solution under nitrogen were added potassium carbonate (184 mg, 1.333 mmol, 4.0 eq), a catalytic amount of NaI and N-tert-butyl-2-chloroacetamide (199 mg, 1.333 mmol, 4.0 eq). The reaction mixture was stirred for 15 hours at 90° C. then treated with 1M HCl (10 ml). After extraction with ethyl acetate, the organic layer was washed with water and brine, and dried over anhydrous Na₂SO₄. The residue after rotary evaporation was purified by column chromatography over silica gel and recrystallization to give the title compound (31 mg, 35.4% yield). ¹H NMR (400 MHz, DMSO-d₆): δ 9.13 (s, 1H), 7.41 (s, 1H), 7.32 (d, J=8.4 Hz, 1H), 7.22 (s, 1H), 7.07 (d, J=8.4 Hz, 1H), 4.92 (s, 2H), 4.39 (s, 2H) and 1.29 (s, 9H) ppm. Mp 149-150° C.

Tert-butyl-N-(1,3-dihydro-1-hydroxy-2,1-benzoxaborol-6-yl)ethylcarbamate (H194)

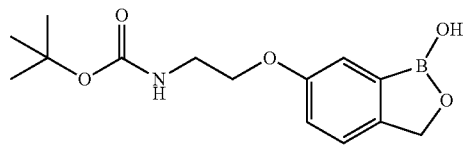 [SMILES: CC(C)(C)OC(=O)NCCOc1ccc2c(c1)B(O)OC2]

The title compound was synthesized using the same condition as that of H193. ¹H NMR (400 MHz, DMSO-d₆): δ 9.13 (s, 1H), 7.30 (d, J=8.4 Hz, 1H), 7.22 (d, J=2.4 Hz, 1H), 7.04 (m, 2H), 4.91 (s, 2H), 3.95 (t, J=6 Hz, 2H), 3.29 (q, J=5.6 & 10.4 Hz, 2H) and 1.38 (s, 9H) ppm. Mp 89-91° C.

N-(2,6-dimethylphenyl)-[2-(1,3-dihydro-1-hydroxy-2,1-benzoxaborol-6-yloxy)]acetamide (H195)

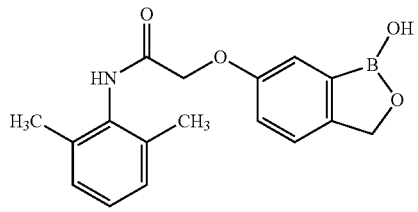 [SMILES: Cc1cccc(C)c1NC(=O)COc1ccc2c(c1)B(O)OC2]

The title compound was synthesized using the same condition as that of H193. ¹H NMR (300 MHz, DMSO-d₆): δ 9.48 (s, 1H), 9.16 (s, 1H), 7.38-7.33 (m, 2H), 7.18 (dd, J=8.1 & 2.7 Hz, 1H), 7.08-7.04 (m, 3H), 4.94 (s, 2H), 4.73 (s, 2H) and 2.10 (s, 6H) ppm. Mp 139-141° C.

6-(2-Methoxyethoxy)-1,3-dihydro-1-hydroxy-2,1-benzoxaborole (H196)

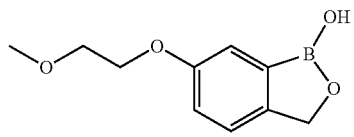

The title compound was synthesized using the same condition as that of H187. ¹H NMR (400 MHz, acetone-d₆): δ 8.01 (s, 1H), 7.32 (d, J=8.4 Hz, 1H), 7.26 (d, J=2.4 Hz, 1H), 7.07 (dd, J=8.4 & 2.4 Hz, 1H), 4.95 (s, 2H), 4.14 (t, J=4.8 Hz, 2H), 3.71 (t, J=4.8 Hz, 2H) and 3.36 (s, 3H) ppm. Mp 68-70° C.

6-(2,2-Dimethoxyethoxy)-1,3-dihydro-1-hydroxy-2,1-benzoxaborole (H197)

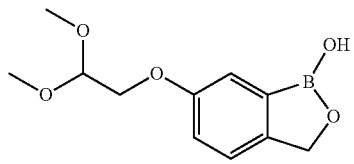 [SMILES: COC(COc1ccc2c(c1)B(O)OC2)OC]

The title compound was synthesized using the same condition as that of H187. ¹H NMR (400 MHz, DMSO-d$_6$): δ 9.11 (s, 1H), 7.31 (d, J=8.4 Hz, 1H), 7.25 (d, J=2.4 Hz, 1H), 7.08 (dd, J=8.4 & 2.4 Hz, 1H), 4.91 (s, 2H), 4.69 (t, J=4.8 Hz, 1H), 3.98 (d, J=5 Hz, 2H) and 3.35 (s, 6H) ppm. Mp 102-104° C.

[2-(1,3-Dihydro-1-hydroxy-2,1-benzoxaborol-6-yloxy)]acetic acid (H198)

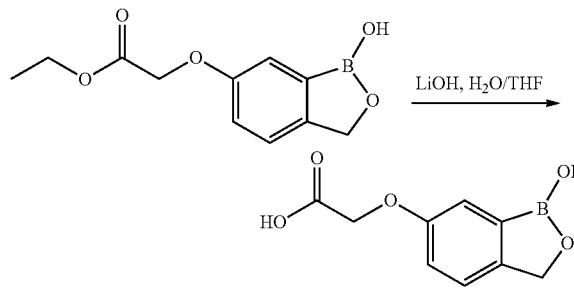

To a solution of H200 (50 mg, 0.21 mmol) in THF (3 mL) was added lithium hydroxide monohydrate (16.8 mg, 0.4 mmol, 2.0 eq) in water (1 mL). The reaction mixture was stirred at room temperature for 40 hours then acidified with 1M HCl (5 mL). The white solid was filtered and washed with water and dried under vacuum to give the title compound (36.6 mg, 88% yield). ¹H NMR (400 MHz, DMSO-d$_6$): δ 12.99 (s, 1H), 9.15 (s, 1H), 7.32 (d, J=8.1 Hz, 1H), 7.19 (d, J=2.4 Hz, 1H), 7.05 (dd, J=8.4 & 2.4 Hz, 1H), 4.92 (s, 2H) and 4.67 (s, 2H) ppm. Mp 166-167° C.

Methyl[2-(1,3-dihydro-1-hydroxy-2,1-benzoxaborol-6-yloxy)]acetate (H199)

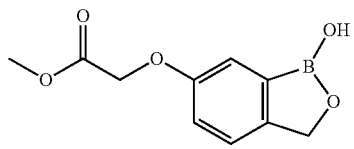 [SMILES: COC(=O)COc1ccc2c(c1)B(O)OC2]

The title compound was synthesized using the same condition as that of H201. ¹H NMR (400 MHz, DMSO-d$_6$): δ 9.15 (s, 1H), 7.32 (d, J=8.4 Hz, 1H), 7.19 (d, J=2.4 Hz, 1H), 7.06 (dd, J=8.4 & 2.7 Hz, 1H), 4.92 (s, 2H), 4.80 (s, 2H) and 3.70 (s, 3H) ppm. Mp 102-104° C.

Ethyl[2-(1,3-dihydro-1-hydroxy-2,1-benzoxaborol-6-yloxy)]acetate (H200)

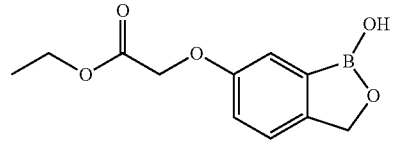 [SMILES: CCOC(=O)COc1ccc2c(c1)B(O)OC2]

H181 (0.667 mmol) was dissolved in DMF (10 mL) and cooled to 0° C. with ice bath. To this solution under nitrogen were added in sequence sodium hydride (106 mg, 2.67 mmol, 4.0 eq) and ethyl 2-chloroacetate (0.284 mL, 2.67 mmol, 4.0 eq). The reaction mixture was stirred for 5 hours then treated with 1M HCl (10 ml). After extraction with ethyl acetate, the organic layer was washed with water and brine, and dried over anhydrous Na$_2$SO$_4$. The residue after rotary evaporation was purified by column chromatography over silica gel to give the title compound (97 mg, 61% yield). ¹H NMR (300 MHz, DMSO-d$_6$): δ 9.14 (s, 1H), 7.32 (d, J=8.1 Hz, 1H), 7.19 (d, J=2.4 Hz, 1H), 7.06 (dd, J=8.4 & 2.7 Hz, 1H), 4.92 (s, 2H), 4.77 (s, 2H), 4.17 (q, J=7.2 Hz, 2H) and 1.21 (t, J=6.9 Hz, 3H) ppm. Mp 96-97° C.

Tert-butyl[2-(1,3-dihydro-1-hydroxy-2,1-benzoxaborol-6-yloxy)]acetate (H201)

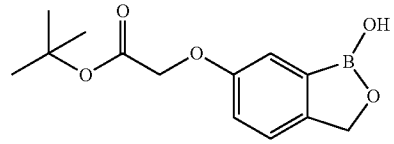 [SMILES: CC(C)(C)OC(=O)COc1ccc2c(c1)B(O)OC2]

H181 (0.667 mmol) was dissolved in DMF (10 mL) and cooled to 0° C. with ice bath. To this solution under nitrogen were added in sequence sodium hydride (106 mg, 2.67 mmol, 4.0 eq) and tert-butyl 2-chloroacetate (0.381 mL, 2.67 mmol, 4.0 eq). The reaction mixture was stirred for 6 hours then treated with 1M HCl (10 ml). After extraction with ethyl acetate, the organic layer was washed with water and brine, and dried over anhydrous Na$_2$SO$_4$. The residue after rotary evaporation was purified by column chromatography over silica gel to give the title compound (66 mg, 37.5% yield). ¹H NMR (400 MHz, DMSO-d$_6$): δ 9.14 (s, 1H), 7.32 (d, J=8.1 Hz, 1H), 7.18 (d, J=2.4 Hz, 1H), 7.04 (dd, J=8.4 & 2.7 Hz, 1H), 4.92 (s, 2H), 4.65 (s, 2H) and 1.42 (s, 9H) ppm. Mp 107-108° C.

[2-(1,3-Dihydro-1-hydroxy-2,1-benzoxaborol-6-yloxy)]acetaldehyde (H202)

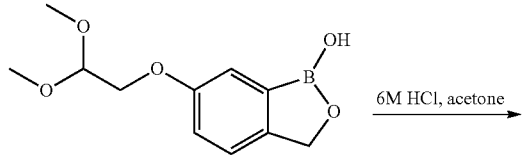

-continued

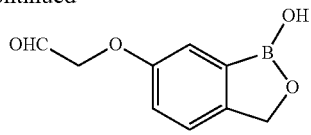

To a solution of H197 (38 mg, 0.16 mmol) in acetone (2 mL) was added 6M HCl (0.3 mL). The reaction mixture was stirred at 30° C. for 24 hours. The residue after evaporation was purified by recrystallization to give the title compound (25.3 mg, 82.5% yield). $^1$H NMR (400 MHz, acetone-$d_6$): δ 9.82 (s, 1H), 7.35 (d, J=8.0 Hz, 1H), 7.23 (d, J=2.4 Hz, 1H), 7.12 (dd, J=8.1 & 2.4 Hz, 1H), 4.96 (s, 2H) and 4.79 (s, 2H) ppm.

Ethyl[2-(1,3-dihydro-1-hydroxy-2,1-benzoxaborol-6-yloxy)] propanoate (H203)

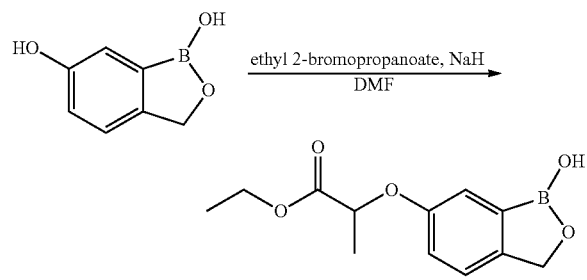

H181 (150 mg, 1.0 mmol) was dissolved in DMF (10.0 mL) and cooled to 0° C. with ice bath. To this solution under nitrogen were added in sequence NaH (60% in mineral oil, 160 mg, 4.0 mmol) and ethyl 2-bromopropanoate (0.51 mL, 4.0 mmol). The reaction mixture was stirred for 1 d then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (144 mg, 7% yield). $^1$H NMR (300 MHz, DMSO-$d_6$): δ 9.18 (s, 1H), 7.31 (d, J=8.1 Hz, 1H), 7.14 (d, J=2.4 Hz, 1H), 7.02 (dd, J=8.4 & 2.7 Hz, 1H), 4.95-4.87 (m, 3H), 4.19-4.08 (m, 2H), 1.51 (d, J=6.6 Hz, 3H) and 1.17 (t, J=7.2 Hz, 3H) ppm; Mp: 65-67° C.

Ethyl[2-(1,3-dihydro-1-hydroxy-2,1-benzoxaborol-6-yloxy)] butanoate (H204)

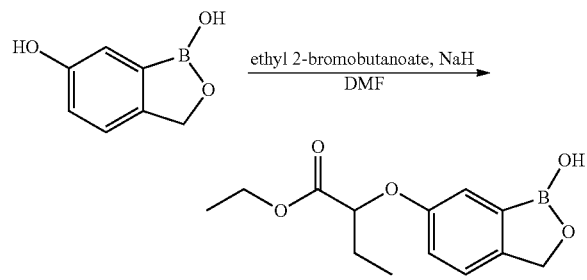

H181 (150 mg, 1.0 mmol) was dissolved in DMF (8.0 mL) and cooled to 0° C. with ice bath. To this solution under nitrogen were added in sequence NaH (60% in mineral oil, 160 mg, 4.0 mmol) and ethyl 2-bromobutanoate (0.59 mL, 4.0 mmol). The reaction mixture was stirred for 1 d then treated with 1 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (165 mg, 62.5% yield). $^1$H NMR (300 MHz, DMSO-$d_6$): δ 9.17 (s, 1H), 7.31 (d, J=8.1 Hz, 1H), 7.16 (d, J=2.4 Hz, 1H), 7.03 (dd, J=8.4 & 2.7 Hz, 1H), 4.91 (s, 2H), 4.73 (t, J=5.4 Hz, 1H), 4.20-4.09 (m, 2H), 1.96-1.83 (m, 2H), 1.17 (t, J=6.9 Hz, 3H) and 1.00 (t, J=7.2 Hz, 3H) ppm; Mp: 90-92° C.

Ethyl[2-(1,3-dihydro-1-hydroxy-2,1-benzoxaborol-6-yloxy)]-2-methylpropanoate (H205)

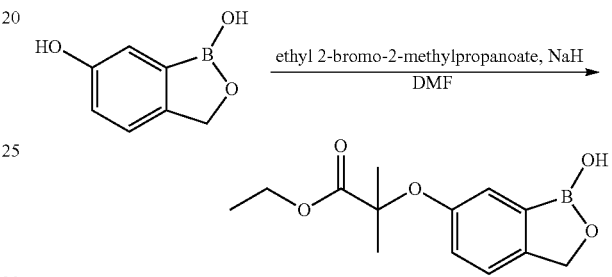

H181 (150 mg, 1.0 mmol) was dissolved in DMF (7.0 mL) and cooled to 0° C. with ice bath. To this solution under nitrogen were added in sequence NaH (60% in mineral oil, 160 mg, 4.0 mmol) and ethyl 2-bromo-2-methylpropanoate (0.59 mL, 4.0 mmol). The reaction mixture was stirred for 1 d then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (161 mg, 61% yield). $^1$H NMR (300 MHz, CDCl$_3$): δ 7.23 (d, J=8.1 Hz, 1H), 7.16 (d, J=2.4 Hz, 1H), 7.04 (dd, J=8.4 & 2.7 Hz, 1H), 5.04 (s, 2H), 4.25 (q, J=6.9 Hz, 2H), 1.60 (s, 6H) and 1.26 (t, J=7.2 Hz, 3H) ppm; Mp: 63-66° C.

Ethyl[2-(1,3-dihydro-1-hydroxy-2,1-benzoxaborol-6-yloxy)]-2-phenylacetate (H206)

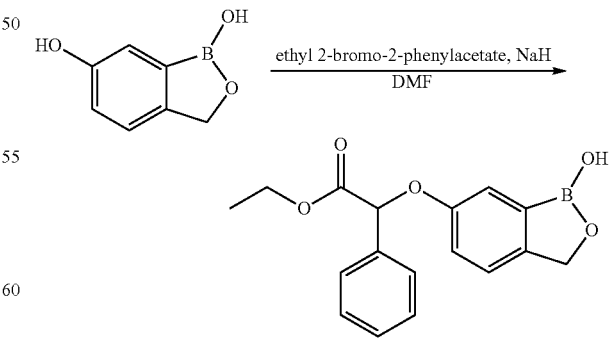

H181 (110 mg, 0.73 mmol) was dissolved in DMF (6.0 mL) and cooled to 0° C. with ice bath. To this solution under nitrogen were added in sequence NaH (60% in mineral oil, 117 mg, 2.93 mmol) and ethyl 2-bromo-2-phenylacetate (0.51 mL, 2.93 mmol). The reaction mixture was stirred for 1 d then treated with 1.0 M HCl (10.0 mL). After extraction with ethyl acetate, the organic layer was washed with water and brine, and dried over anhydrous $Na_2SO_4$. The residue after rotary evaporation was purified by column chromatography over silica gel to give the title compound (136 mg, 60% yield). $^1$H NMR (300 MHz, CDCl$_3$): δ 7.62-7.56 (m, 2H), 7.44-7.12 (m, 6H), 5.67 (s, 1H), 5.03 (s, 2H), 4.30-4.10 (m, 2H) and 1.20 (t, J=7.2 Hz, 3H) ppm; Mp: 94-97° C.

1-(1,3-Dihydro-1-hydroxy-2,1-benzoxaborol-6-yloxy) butan-2-one (H207)

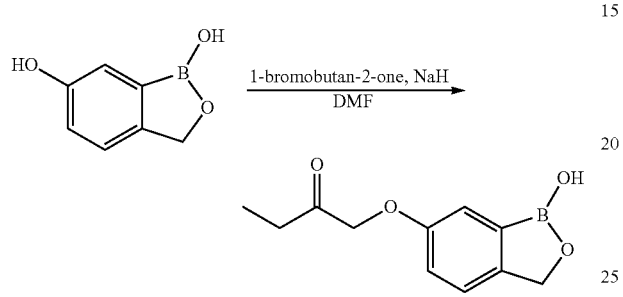

The experimental procedure is similar to the synthesis of H200. Yield: 30%. $^1$H NMR (300 MHz, CDCl$_3$): δ 7.24 (d, J=8.1 Hz, 1H), 7.09 (d, J=2.4 Hz, 1H), 7.05 (dd, J=8.4 & 2.7 Hz, 1H), 5.02 (s, 2H), 4.57 (s, 2H), 2.60 (q, J=7.2 Hz, 2H) and 1.08 (t, J=7.5 Hz, 3H) ppm; Mp: 83-85° C.

1-(1,3-Dihydro-1-hydroxy-2,1-benzoxaborol-6-yloxy) pentan-2-one (H208)

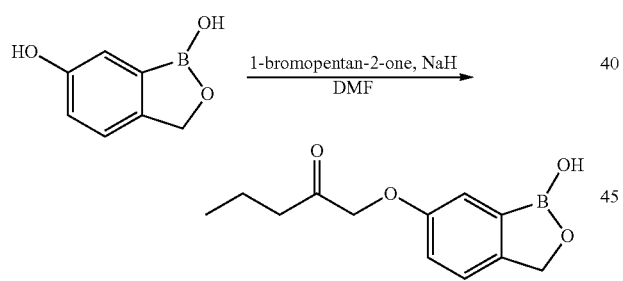

The experimental procedure is similar to the synthesis of H200. Yield: 33.6%. $^1$H NMR (400 MHz, CD$_3$COCD$_3$): δ 9.14 (s, 1H), 7.33 (d, J=8.1 Hz, 1H), 7.19 (d, J=2.4 Hz, 1H), 7.08 (dd, J=8.4 & 2.7 Hz, 1H), 4.96 (s, 2H), 4.73 (s, 2H), 2.57 (t, J=7.2 Hz, 2H), 1.66-1.55 (m, 2H), and 0.92 (t, J=7.6 Hz, 3H) ppm; Mp: 107-109° C.

1-(1,3-Dihydro-1-hydroxy-2,1-benzoxaborol-6-yloxy)-4-methylpentan-2-one (H209)

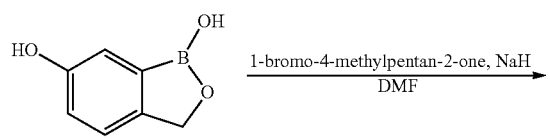

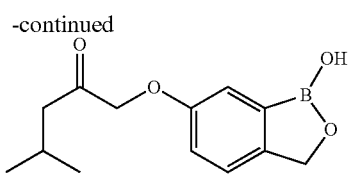

The experimental procedure is similar to the synthesis of H200. Yield: 45%. $^1$H NMR (400 MHz, DMSO-d$_6$): δ 9.14 (s, 1H), 7.31 (d, J=8.1 Hz, 1H), 7.15 (d, J=2.4 Hz, 1H), 7.03 (dd, J=8.4 & 2.7 Hz, 1H), 4.91 (s, 2H), 4.78 (s, 2H), 2.40 (d, J=7.2 Hz, 2H), 2.15-2.02 (m, 1H), and 0.88 (t, J=6.8 Hz, 6H) ppm; Mp: 107-108° C.

3-(1,3-Dihydro-1-hydroxy-2,1-benzoxaborol-6-yloxy) butan-2-one (H210)

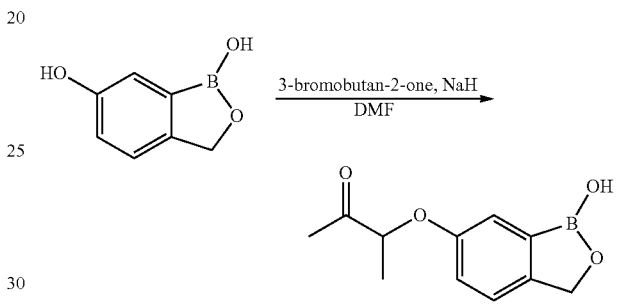

The experimental procedure is similar to the synthesis of H200. Yield: 62.3%. $^1$H NMR (400 MHz, CDCl$_3$): δ 7.25 (d, J=8.1 Hz, 1H), 7.10 (d, J=2.4 Hz, 1H), 7.02 (dd, J=8.4 & 2.7 Hz, 1H), 5.04 (s, 2H), 4.66 (q, J=6.8 Hz, 1H), 2.19 (s, 3H) and 1.51 (d, J=7.2 Hz, 3H) ppm; Mp: 90-92° C.

2-(1,3-Dihydro-1-hydroxy-2,1-benzoxaborol-6-yloxy) pentan-3-one (H211)

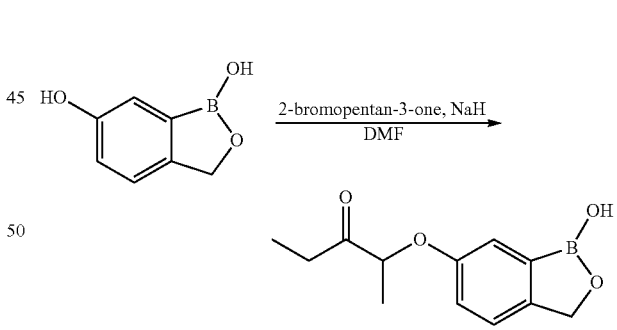

H181 (150 mg, 1.0 mmol) was dissolved in DMF (6.0 mL) and cooled to 0° C. with ice bath. To this solution under nitrogen were added in sequence NaH (60% in mineral oil, 160 mg, 4.0 mmol) and 2-bromopentan-3-one (660.12 mg, 4.0 mmol). The reaction mixture was stirred for 1 d then treated with 1.0 M HCl (10.0 mL). After extraction with ethyl acetate, the organic phase was washed with water and brine, and dried over anhydrous $Na_2SO_4$. The residue after rotary evaporation was purified by column chromatography over silica gel to give the title compound (88.9 mg, 38% yield). $^1$H NMR (400 MHz, CDCl$_3$): δ 7.21 (d, J=8.1 Hz, 1H), 7.06 (d, J=2.4 Hz, 1H), 6.98 (dd, J=8.4 & 2.7 Hz, 1H), 5.00 (s, 2H), 4.67 (q, J=6.8 Hz, 1H), 2.73-2.61 (m, 1H), 2.49-2.39 (m, 1H), 1.47 (d, J=6.8 Hz, 3H) and 0.99 (t, J=7.2 Hz, 3H) ppm; Mp: 72-74° C.

3-(1,3-Dihydro-1-hydroxy-2,1-benzoxaborol-6-yloxy) pentan-2-one (H212)

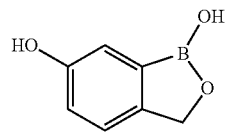

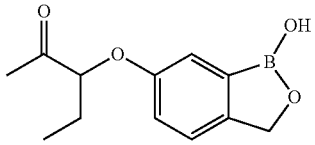

The experimental procedure is similar to the synthesis of H200. Yield: 50.9%. $^1$H NMR (400 MHz, DMSO-d$_6$): δ 9.14 (s, 1H), 7.31 (d, J=8.1 Hz, 1H), 7.12 (d, J=2.4 Hz, 1H), 7.04 (dd, J=8.4 & 2.7 Hz, 1H), 4.91 (s, 2H), 4.67-4.61 (m, 1H), 2.14 (s, 3H), 1.91-1.78 (m, 2H) and 0.96 (t, J=7.6 Hz, 3H) ppm; Mp: 68-70° C.

3-(1,3-Dihydro-1-hydroxy-2,1-benzoxaborol-6-yloxy) hexan-2-one (H213)

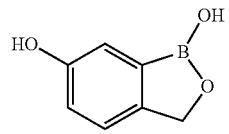

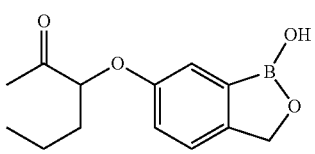

The experimental procedure is similar to the synthesis of H200. Yield: 50.4%. $^1$H NMR (300 MHz, CDCl$_3$): δ 7.23 (d, J=8.1 Hz, 1H), 7.07 (d, J=2.4 Hz, 1H), 7.00 (dd, J=8.4 & 2.7 Hz, 1H), 5.02 (s, 2H), 4.52-4.44 (m, 1H), 2.13 (s, 3H), 1.91-1.71 (m, 2H), 1.59-1.45 (m, 2H) and 0.94 (t, J=7.2 Hz, 3H) ppm; Oil.

3-(1,3-Dihydro-1-hydroxy-2,1-benzoxaborol-6-yloxy) heptan-4-one (H214)

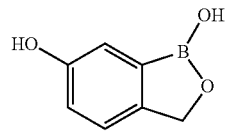

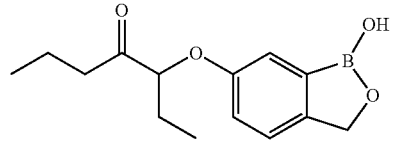

The experimental procedure is similar to the synthesis of H200. Yield: 45%. $^1$H NMR (400 MHz, CDCl$_3$): δ 7.21 (d, J=8.1 Hz, 1H), 7.07 (d, J=2.4 Hz, 1H), 6.99 (dd, J=8.4 & 2.7 Hz, 1H), 4.99 (s, 2H), 4.45-4.44 (m, 1H), 2.61-2.51 (m, 1H), 2.40-2.30 (m, 1H), 1.90-1.78 (m, 2H), 1.57-1.47 (m, 2H), 1.03-0.98 (m, 3H) and 0.85-0.79 (m, 3H) ppm; Oil.

3-(1,3-Dihydro-1-hydroxy-2,1-benzoxaborol-6-yloxy)-4-methyl-pentan-2-one (H215)

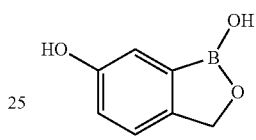

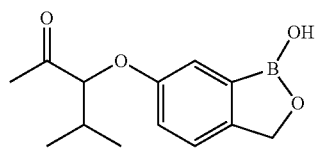

The experimental procedure is similar to the synthesis of H200. Yield: 16%. $^1$H NMR (400 MHz, CDCl$_3$): δ 7.21 (d, J=8.1 Hz, 1H), 7.06 (d, J=2.4 Hz, 1H), 6.99 (dd, J=8.4 & 2.7 Hz, 1H), 5.00 (s, 2H), 4.19 (d, J=6 Hz, 1H), 2.22-2.15 (m, 1H), 2.10 (s, 3H), 1.05 (d, J=6.8 Hz, 3H) and 0.98 (d, J=6.8 Hz, 3H) ppm; Mp: 58-59° C.

3-(1,3-Dihydro-1-hydroxy-2,1-benzoxaborol-6-yloxy)-3-methylbutan-2-one (H216)

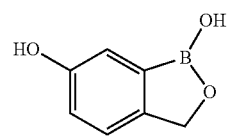

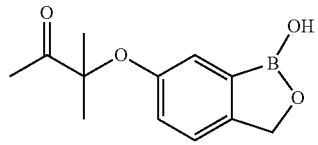

The experimental procedure is similar to the synthesis of H200. Yield: 25.6%. $^1$H NMR (400 MHz, CDCl$_3$): δ 7.20 (d, J=8.1 Hz, 1H), 7.05 (d, J=2.4 Hz, 1H), 6.93 (dd, J=8.4 & 2.7 Hz, 1H), 5.00 (s, 2H), 2.27 (s, 3H) and 1.44 (s, 6H) ppm; Oil.

6-(2-Hydroxy-1-methylbutoxy)-1,3-dihydro-1-hydroxy-2,1-benzoxaborole (H217)

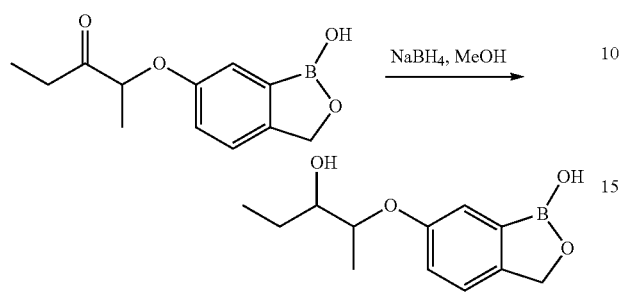

H211 (75 mg, 0.32 mmol) was dissolved in MeOH (3 mL) and cooled to 0° C. with ice bath. To this solution was added NaBH$_4$ (18.1 mg, 0.48 mmol). The reaction mixture was stirred for 2 h then treated with saturated HCl (1 M). After evaporation, the residue was extracted with ethyl acetate and the organic layer was washed with water and brine. The residue after rotary evaporation was purified by preparative TLC to give the title compound (45 mg, 59% yield). $^1$H NMR (400 MHz, CD$_3$OD): δ 7.23 (d, J=8.1 Hz, 1H), 7.16 (d, J=2.4 Hz, 1H), 7.05 (dd, J=8.4 & 2.7 Hz, 1H), 4.97 (s, 2H), 4.37-4.25 (m, 1H), 4.62-4.50 (m, 1H), 1.71-1.40 (m, 2H), 1.25 (t, J=6 Hz, 3H) and 1.02-0.95 (m, 3H) ppm; Oil.

6-((Isoindoline-1,3-dione-2-yl)propoxy)-1,3-dihydro-1-hydroxy-2,1-benzoxaborole (H218)

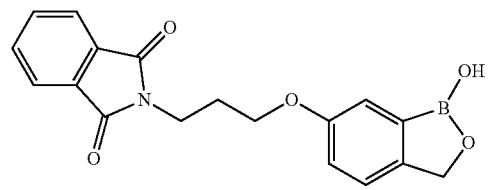 [SMILES: O=C1c2ccccc2C(=O)N1CCCOc1ccc2c(c1)B(O)OC2]

The title compound was synthesized using the same condition as that of H187. $^1$H NMR (300 MHz, DMSO-d$_6$): δ 9.01 (s, 1H), 7.84 (d, J=2.7 Hz, 4H), 7.24 (d, J=8.4 Hz, 1H), 7.17 (d, J=2.4 Hz, 1H), 6.87 (dd, J=8.4 & 2.4 Hz, 1H), 4.89 (s, 2H), 4.01 (t, J=6.2 Hz, 2H), 3.77 (t, J=6.5 Hz, 2H) and 2.12-2.02 (m, 2H) ppm. Mp 159-162° C.

[3-(1,3-Dihydro-1-hydroxy-2,1-benzoxaborol-6-yloxy)]propanoic acid (H219)

The title compound may be prepared by the following scheme. Ethyl[3-(1,3-dihydro-1-hydroxy-2,1-benzoxaborol-6-yloxy)]propanoate

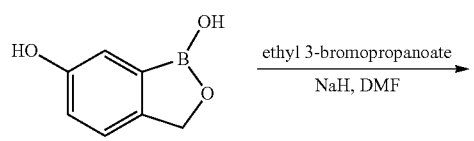

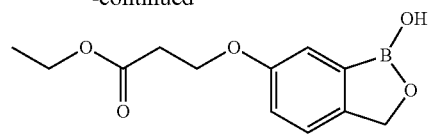

[4-(1,3-Dihydro-1-hydroxy-2,1-benzoxaborol-6-yloxy]butanoic acid (H220)

The title compound may be prepared by the following scheme.

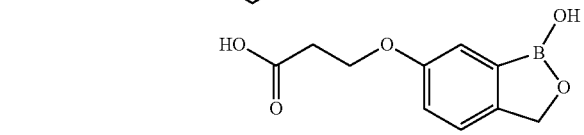

[5-(1,3-Dihydro-1-hydroxy-2,1-benzoxaborol-6-yloxy]pentanoic acid (H221)

The title compound may be prepared by the following scheme.

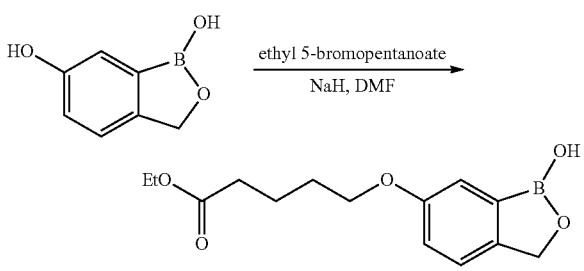

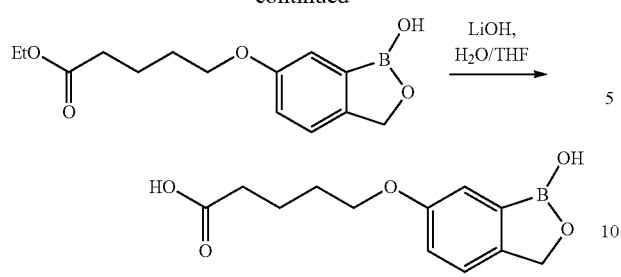

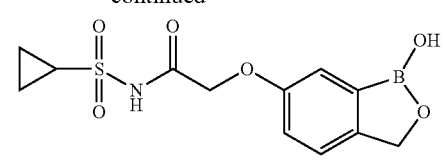

6-(2-(1H-Tetrazol-5-yl)oxymethyl)benzo[c][1,2]oxaborol-1(3H)-ol (H222)

The title compound may be prepared by the following scheme.

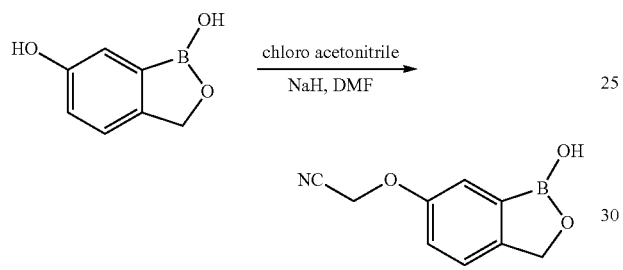

5-(1-Hydroxy-1,3-dihydrobenzo[c][1,2]oxaborol-6-yloxy)thiazolidine-2,4-dione (H224)

The title compound may be prepared by the following scheme.

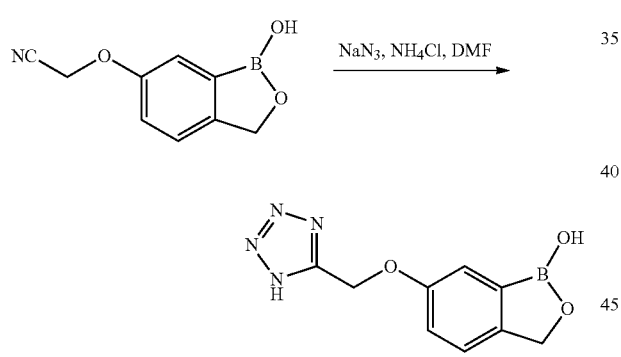

2-(1-Hydroxy-1,3-dihydrobenzo[c][1,2]oxaborol-6-yloxy)-N-(cyclopropylsulfonyl) acetamide (H223)

The title compound may be prepared by the following scheme.

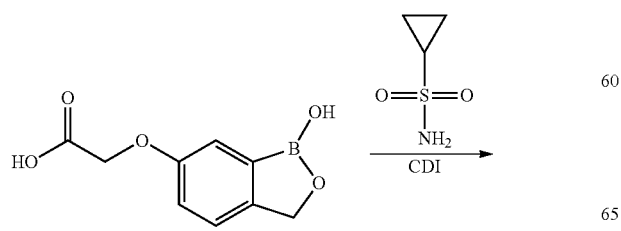

5-((1-Hydroxy-1,3-dihydrobenzo[c][1,2]oxaborol-6-yloxy)methyl)thiazolidine-2,4-dione (H225)

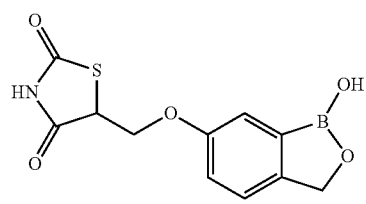 [SMILES: O=C1NC(=O)C(COc2ccc3c(c2)B(O)OC3)S1]

The title compound may be prepared by the following scheme.

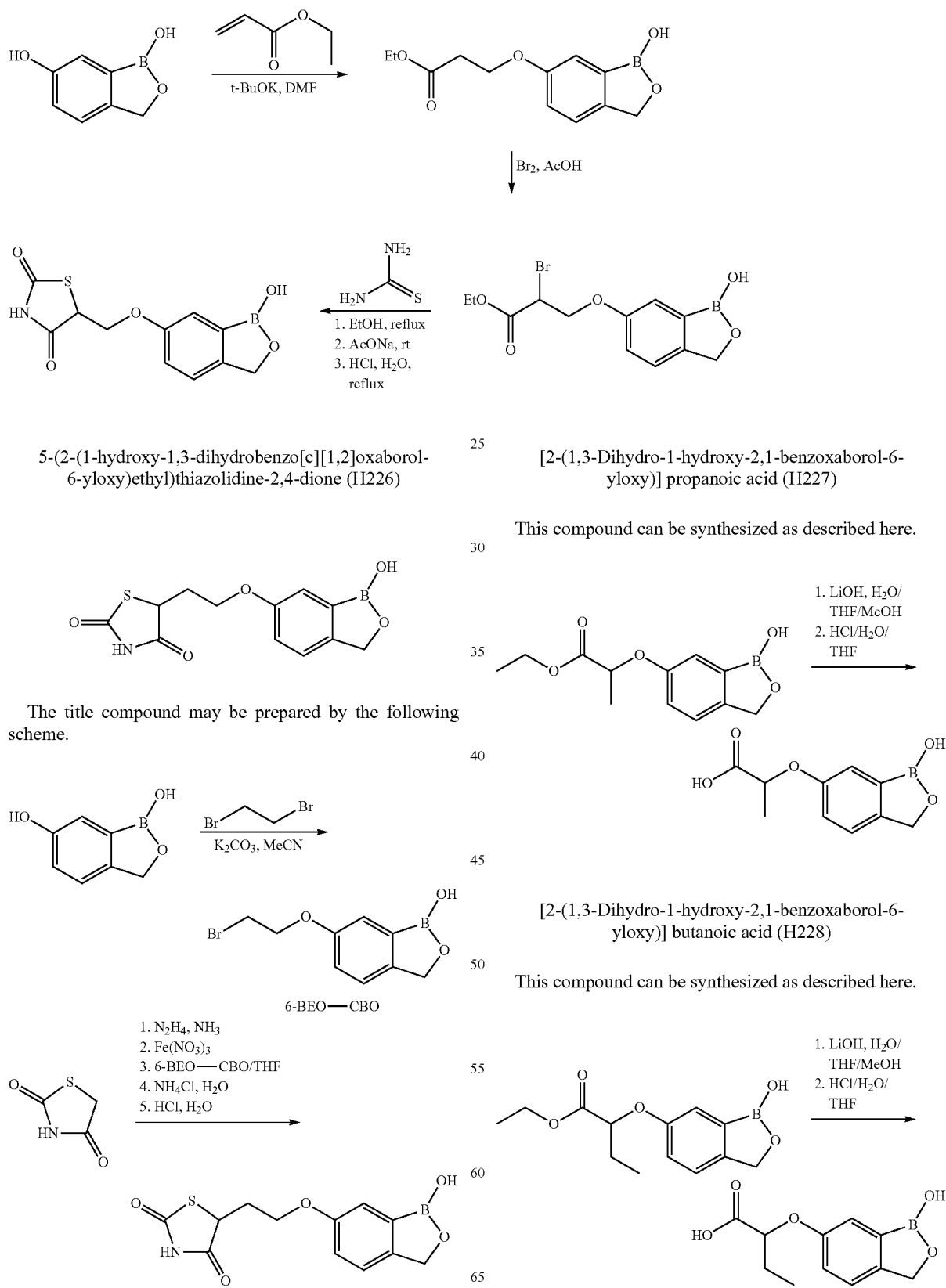

5-(2-(1-hydroxy-1,3-dihydrobenzo[c][1,2]oxaborol-6-yloxy)ethyl)thiazolidine-2,4-dione (H226)

The title compound may be prepared by the following scheme.

[2-(1,3-Dihydro-1-hydroxy-2,1-benzoxaborol-6-yloxy)] propanoic acid (H227)

This compound can be synthesized as described here.

[2-(1,3-Dihydro-1-hydroxy-2,1-benzoxaborol-6-yloxy)] butanoic acid (H228)

This compound can be synthesized as described here.

[2-(1,3-Dihydro-1-hydroxy-2,1-benzoxaborol-6-yloxy)]-2-methylpropanoic acid (H229)

This compound can be synthesized as described here.

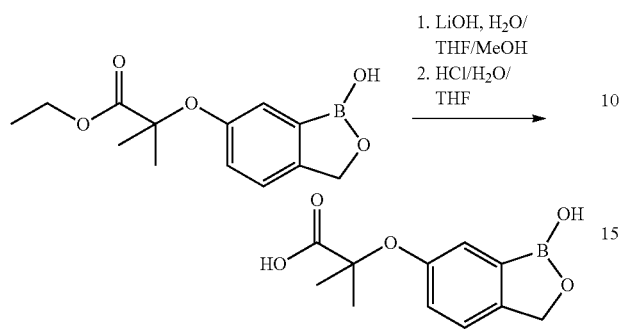

[2-(1,3-Dihydro-1-hydroxy-2,1-benzoxaborol-6-yloxy)]-2-phenylacetic acid (H230)

This compound can be synthesized as described here.

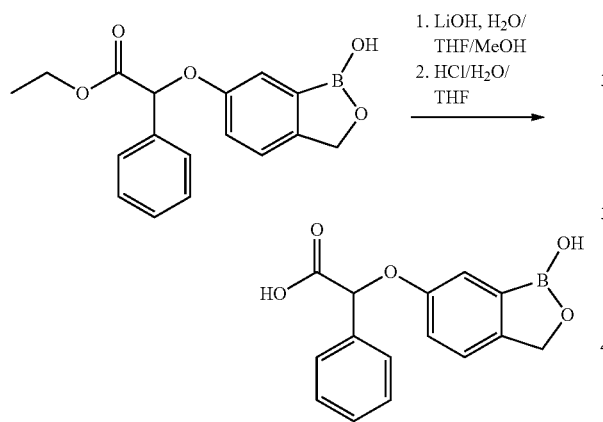

Example 2

*Trypanosoma brucei brucei* High-Throughput Screening Assay Procedure

Experiments were conducted with the bloodstream-form trypanosome *T. brucei brucei* 5427 strain and the *T. brucei brucei* STIB 795 strain. Parasites were cultured in T-25 vented cap flasks and kept in humidified incubators at 37° C. and 5% $CO_2$. The parasite culture media was complete HMI-9 medium (c.f. Hirumi, *Journal of Parasitology*, 40:75, 985-989 (1989)) containing 10% FBS, 10% Serum Plus medium and penicillin/streptomycin. To ensure log growth phase, trypanosomes were sub-cultured at appropriate dilutions every 2-3 days.

In Vitro Drug Sensitivity Assays

Log phase cultures were diluted 1:10 in HMI-9 and 10 uL was counted using hemocytometer to determine parasite concentration. Parasites were diluted to $2\times10^5$/mL in HMI-9 to generate a 2-fold working concentration for assay. Compounds to be tested were serially diluted in DMSO and 0.5 uL added to 49.5 uL HMI-9 in triplicate 96-well plates using a Biomek NX liquid handler. Parasites from the diluted stock were added to each well (50 uL) using a Multidrop 384 dispenser to give a final concentration of $1.0\times10^5$/ml parasites in 0.4% for DMSO. Trypanosomes were incubated with compounds for 72 hrs at 37° C. with 5% $CO_2$. Resazurin (20 uL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Results are provided in FIG. 1.

Example 3

*Trypanosoma cruzi* C2C4 Screening Assay Procedure

Rat skeletal myoblasts (L-6 cells) can be seeded in 96-well microtitre plates at $2\times10^3$ cells/well in 100 μL RPMI 1640 medium with 10% FBS and 2 mM L-glutamine. After 24 h the medium can be removed and replaced by 100 μl per well containing $5\times10^3$ trypomastigote forms of *T. cruzi* Tulahuen strain C2C4 containing the β-galactosidase (Lac Z) gene (Buckner, et al., *Antimicrobial Agents and Chemotherapy*, 40: 2592-2597 (1996)). After 48 h the medium can be removed from the wells and replaced by 100 μl fresh medium with or without a serial drug dilution of seven 3-fold dilution steps covering a range from 90 to 0.123 μg/ml. After 96 h of incubation the plates can be inspected under an inverted microscope to assure growth of the controls and sterility. The substrate (50 μl) chlorophenol red-β-D-galactopyranoside (CPRG, Roche Diagnostics Ltd) in 0.25% Nonidet P-40/PBS can be added to all wells and a color reaction developed within 2-6 h. which can be read photometrically at 540 nm. Data can be transferred into the graphic programme Softmax Pro (Molecular Devices), which calculated 1050 values.

Example 4

Trypanosoma cruzi CL2 Screening Assay Procedure

Parasite and Cell Cultures.

*Trypanosoma cruzi*, Tulahuen CL2, β galactosidase strain (nifurtimox-sensitive) was used (Buckner et al., *Antimicrob Agents Chemother.* 40: 2592-2597 (1996)). The strain was maintained in MRC-5SV2 (human lung fibroblast) cells. A SV-40 transformed cell line was available to obtain unlimited subcultivation characteristics in MEM medium, supplemented with 200 mM. L-glutamine, 16.5 mM $NaHCO_3$, and 5% inactivated fetal calf serum. All cultures and assays were conducted at 37° C. with 5% $CO_2$.

Compound Solutions/Dilutions. Compound stock solutions were prepared in 100% DMSO at 20 mM or mg/ml for natural products, drug mixtures and if the molecular weight was not known. The compounds were serially pre-diluted (2-fold or 4-fold) in DMSO followed by a further (intermediate) dilution in demineralized water to assure a final in-test DMSO concentration of <1%.

Drug Sensitivity Assays. Assays were performed in sterile 96-well microtiter plates, each well containing 10 μl of the watery compound dilutions together with 190 μl of MRC-5 cell/parasite inoculum ($4\times10^3$ cells/well+$4\times10^4$ parasites/well). Parasite growth was compared to untreated-infected controls (100% growth) and noninfected controls (0% growth) after 7 days incubation at 37° C. and 5% $CO_2$. Parasite burdens were assessed after adding the substrate CPRG (chlorophenolred β-D-galactopyranoside): 50 μl/well of a stock solution containing 15.2 mg CPRG+250 μl Nonidet in 100 ml PBS. The change in color was measured spectrophotometrically at 540 nm after 4 hours incubation at 37° C. The results were expressed as % reduction in parasite burdens compared to control wells and an IC50 (50% inhibitory concentration) was calculated.

Primary Screen. *Trypanosoma cruzi* β galactosidase strain was used. Compounds were tested at 5 concentrations (64-16-4-1 and 0.25 μM or ug/ml). Nifurtimox or benznidazole were included as the reference drugs. The test compound was classified as inactive when the $IC_{50}$ was higher than 30 μM. When the IC50 was between 30 and 5 μM, the compound was regarded as being moderate active. When the $IC_{50}$ was lower than 5 μM, the compound was classified as highly active on the condition that it also demonstrated selective action (absence of cytotoxicity). A final recommendation for activity was given after confirmatory evaluation in a secondary screening.

Secondary Screen. *Trypanosoma cruzi* β galactosidase strain was used and IC50-values were determined using an extended dose range (2-fold compound dilutions). Nifurtimox or benznidazole was included as reference drugs. Advanced selectivity evaluation was performed against a panel of unrelated organisms (bacteria, yeasts, fungi and other protozoan parasites).

Results from this assay are provided in FIG. 1.

Example 5

*Trypanosome brucei gambiense* Screening Assay Procedure

The following *T. b. gambiense* strains can be isolated from sleeping sickness patients as described, and can be subsequently propagated in mice at Swiss Tropical Institute.

*T. b. gambiense* 40R, 108R were isolated by Pati Pyana in Mbuji Mayi (D. R Congo) in 2005 and then propagated in STI (Swiss Tropical Institute, Basel, Switzerland) in different mice in winter 2006.
  40R is a relapse 6 months after a 10 days melarsoprol treatment.
  108R is a relapse 8 months after a 10 days melarsoprol treatment
*T. b. gambiense* DAL 1402 was obtained from the cryobank of the "Project de Recherches Cliniques Sur la Trypanosomiase," in Daloa. It was isolated in 1990 from a human patient in Cote d'Ivoire.
*T. b. gambiense* ITMAP 141267 was isolated in Bandundu/Lac Mai-Ndombe, DRC, 1960
*T. b. gambiense* Drani was isolated from a patient in Uganda; West. Nile, 1995; original stabilate ID: UTRO 210396 A.

In Vitro Culture and Assay Procedure: 50 μA HMI-9 medium (Hirumi et al., *J. Parasitology*, 75: 985-989 (1989)) supplemented 10% heat inactivated fetal calf serum and 5% heat inactivated human serum can be added to each well of a 96-well microtiter plate. Serial drug dilutions of seven 3-fold dilution steps covering a range from 90 to 0.123 μg/ml were prepared. Then $2\times10^5$ bloodstream forms of *T. b. gambiense* in 50 μA medium can be added to each well and the plate incubated at 37° C. under a 5% $CO_2$ atmosphere for 72 h. 10 μA Alamar Blue (resazurin, 12.5 mg in 100 ml double-distilled water) can then be added to each well and incubation can continue for a further 2-4 h (Raz et al, *Acta Trop* 68:139-47 (1997)). Then the plates can be read with a Spectramax Gemini XS microplate fluorometer (Molecular Devices Cooperation, Sunnyvale, Calif., USA) using an excitation wave length of 536 nm and an emission wave length of 588 nm. Data ca be analyzed using the microplate reader software Softmax Pro (Molecular Devices Cooperation, Sunnyvale, Calif., USA).

Example 6

*Trypanosoma brucei rhodesiense* STIB 900 Screening Assay Procedure

The *Trypanosoma brucei rhodesiense* STIB900 strain was isolated in 1982 from a human patient in Tanzania and after several mouse passages cloned and adapted to axenic culture conditions (Baltz, et al., *EMBO Journal* 4:1273-1277 (1985); Thuita, et al., *Acta Tropica* 108:6-10 (2008)). Minimum Essential Medium (50 μl) supplemented with 25 mM HEPES, 1 g/L additional glucose, 1% MEM non-essential amino acids (100×), 0.2 mM 2-mercaptoethanol, 1 mM Na-pyruvate and 15% heat inactivated horse serum was added to each well of a 96-well microtiter plate. Serial drug dilutions of seven 3-fold dilution steps covering a range from 90 to 0.123 μg/ml were prepared. Then $10^4$ bloodstream forms of T. b. rhodesiense STIB 900 in 50 μl was added to each well and the plate incubated at 37° C. under a 5% $CO_2$ atmosphere for 72 h. 10 μl Alamar Blue (resazurin, 12.5 mg in 100 ml double-distilled water) was then added to each well and incubation continued for a further 2-4 h (Raz, et al., *Acta Trop* 68:139-47 (1997)). Then the plates were read with a Spectramax Gemini XS microplate fluorometer (Molecular Devices Cooperation, Sunnyvale, Calif., USA) using an excitation wave length of 536 nm and an emission wave length of 588 nm. Data were analyzed using the microplate reader software Softmax Pro (Molecular Devices Cooperation, Sunnyvale, Calif., USA).

Results from this assay are provided in FIG. 1.

Example 7

*Leishmania donovani* Axenic Amastigote Screening Assay Procedure

Amastigotes of *L. donovani* strain MHOM/ET/67/L82 can be grown in axenic culture at 37° C. in SM medium (Cunningham, I. *J Protozol*. 24:325-329 (1977)) at pH 5.4 supplemented with 10% heat-inactivated fetal bovine serum under an atmosphere of 5% $CO_2$ in air. One hundred microlitres of culture medium with $10^5$ amastigotes from axenic culture with or without a serial drug dilution can be seeded in 96-well microtitre plates. Serial drug dilutions of seven 3-fold dilution steps covering a range from 90 to 0.123 μg/ml can be prepared. After 72 h of incubation the plates can be inspected under an inverted microscope to assure growth of the controls and sterile conditions. 10 μl of Alamar Blue (12.5 mg resazurin dissolved in 100 ml distilled water) (Mikus and Steverdig, *Parasitology International* 48:265-269 (2000)) can be then added to each well and the plates incubated for another 2 h. Then the plates can be read with a Spectramax Gemini XS microplate fluorometer (Molecular Devices Cooperation, Sunnyvale, Calif., USA) using an excitation wave length of 536 nm and an emission wave length of 588 nm. Data can be analyzed using the software Softmax Pro (Molecular Devices Cooperation, Sunnyvale, Calif., USA). Decrease of fluorescence (=inhibition) can be expressed as percentage of the fluorescence of control cultures and plotted against the drug concentrations. From the sigmoidal inhibition curves $IC_{50}$ values can be calculated.

Example 8

*Leishmania donovani* Macrophage and *Leishmania infantum* Macrophage Screening Assay Procedure Parasite and Cell Cultures. Two *Leishmania* species (*L. infantum* MHOM/MA(BE)/67 and *L. donovani* MHOM/ET/67/L82) were used. The strains were maintained in the Golden Hamster (*Mesocricetus auratus*). Amastigotes were collected from the spleen of an infected donor hamster using three centrifugation purification steps (300 rpm, keeping the supernatant, 2200 rpm, keeping the supernatants and 3500 rpm, keeping the pellet) and spleen parasite burdens were assessed using the Stauber technique (Stauber L A., *Exp Parasitol.* 18: 1-11 (1966)). Primary peritoneal mouse macrophages were used as host cell and were collected 2 days after peritoneal stimulation with a 2% potato starch suspension. All cultures and assays were conducted at 37° C. under an atmosphere of 5% $CO_2$.

Compound Solutions/Dilutions. Compound stock solutions were prepared in 100% DMSO at 20 mM or mg/ml. Concentrations were standard and expressed in molar concentrations, except for natural products, drug mixtures and if the molecular weight was not known. The compounds were serially pre-diluted (2-fold or 4-fold) in DMSO followed by a further (intermediate) dilution in demineralized water to assure a final in-test DMSO concentration of <1%.

Drug Sensitivity Assays. Assays were performed in 96-well microtiter plates, each well contained 10 µl of the compound dilutions together with 190 µl of macrophage/parasite inoculum ($3 \times 10^3$ cells+$4.5 \times 10^5$ parasites/well). The inoculum was prepared in RPMI-1640 medium, supplemented with 200 mM L-glutamine, 16.5 mM $NaHCO_3$, and 5% heat-inactivated fetal calf serum. Parasite multiplication was compared to untreated-infected controls (100% growth) and uninfected controls (0% growth). After 5 days incubation, parasite burdens (mean number of amastigotes/macrophage) were microscopically assessed after staining the cells with a 10% Giemsa solution. The results were expressed as % reduction in parasite burden compared to untreated control wells and an $IC_{50}$ (50% inhibitory concentration) was calculated.

Primary Screen. *Leishmania infantum* MHOM/MA(BE)/67 strain was used. The compounds were tested at 5 concentrations (64-16-4-1 and 0.25 µM or µg/ml). Sodium-stibogluconate ($IC_{50}$=8.7+2.1 µM) and miltefosin ($IC_{50}$=4.3+1.1 µM) were included as the reference drugs. A test compound was classified as inactive when the $IC_{50}$ was higher than 30 µM. When the $IC_{50}$ was between 30 and 10 µM, the compound was regarded as moderately active. If the $IC_{50}$ is lower than 10 µM, the compound was classified as highly active on the condition that it also demonstrates selective action (absence of cytotoxicity against primary peritoneal macrophages). A final recommendation for activity was given after confirmatory evaluation in a secondary screening.

Secondary Screen. *Leishmania infantum* MHOM/MA(BE)/67 and *L. donovani* MHOM/ET/67/L82 strains were used and the $IC_{50}$-values were determined using an extended dose range (2-fold compound dilutions). Pentostam®, miltefosine, fungizone and PX-6518 were included as reference drugs. Advanced selectivity evaluations were performed against a panel of unrelated organisms (bacteria, yeasts, fungi and other protozoan parasites).

Results from this assay are provided in FIG. 1.

Example 9

*Plasmodium falciparum* Screening Assay Procedure

In vitro activity against erythrocytic stages of *P. falciparum* was determined using a $^3$H-hypoxanthine incorporation assay (Desjardins et al., Antimicrobial Agents and Chemotherapy 16:710-718 (1979), Matiel and Pink. *Plasmodium falciparum* malaria parasite cultures and their use in immunology. In I. Lefkovits and B. Perris (ed.), Immunological Methods. Academic Press, San Diego(1990)), using the chloroquine and pyrimethamine resistant K1 strain that originate from Thailand (Thaitong et al. Transactions of the Royal Society of Tropical Medicine and Hygiene 77:228-231 (1983)) and the standard drug chloroquine (Sigma C6628). Compounds can be dissolved in DMSO at 10 mg/ml and can be added to parasite cultures incubated in RPMI 1640 medium without hypoxanthine, supplemented with HEPES (5.94 g/l), $NaHCO_3$ (2.1 g/l), neomycin (100 U/ml), Albumax$^R$ (5 g/l) and washed human red cells A$^+$ at 2.5% haematocrit (0.3% parasitaemia). Serial drug dilutions of seven 2-fold dilution steps covering a range from 5 to 0.156 µg/ml can be prepared. The 96-well plates can be incubated in a humidified atmosphere at 37 C; 4% $CO_2$, 3% $O_2$, 93% $N_2$. After 48 h 50 µl of $^3$H-hypoxanthine (=0.5 µCi) was added to each well of the plate. The plates can be incubated for a further 24 h under the same conditions. The plates can be then harvested with a Betaplate™ cell harvester (Wallac, Zurich, Switzerland), and the red blood cells transferred onto a glass fibre filter then washed with distilled water. The dried filters can be inserted into a plastic foil with 10 ml of scintillation fluid, and counted in a Betaplate™ liquid scintillation counter (Wallac, Zurich, Switzerland). $IC_{50}$ values can be calculated from sigmoidal inhibition curves using Microsoft Excel.

Example 10

*Trypanosoma brucei leucyl*-tRNA Synthetase Aminoacylation Inhibition Assay Procedure Compounds were dissolved in DMSO. Experiments were performed in 70 µL reaction mixtures containing: 50 mM HEPES-KOH (pH 7.8), 5 mM $MgCl_2$, 45 mM KCl, 1 mM DTT, 0.02% BSA (WN), 0.4 mg/ml brewer's yeast tRNA, 4 mM ATP, 10 µM [$^{14}$C]Leu, 2 nM *T. brucei* LeuRS and 7 µL compounds at indicated concentrations. The reaction mixture without ATP was first pre-incubated at 37° C. for 20 minutes and then the reaction was initiated by adding ATP to 4 mM at 37° C. for another 20 min. Three aliquots of 20 µL of reaction solution were quenched on three pieces of Whatman qualitative filter paper separately with 5% trichloroacetic acid (TCA). Each filter was washed three times for 10 min each with 5% TCA and then three times for 10 min each with 95% ethanol. Each filter was then dried under an infrared heat lamp for 20 min. The radioactivity of the precipitate was quantified by a scintillation counter (Beckman Coulter).

Results from this assay are provided in FIG. 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the following formula:

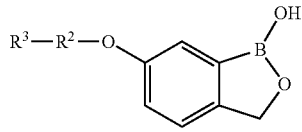

or a salt, hydrate, or solvate thereof,
wherein
- $R^2$ is selected from the group consisting of unsubstituted linear alkylene, alkylene substituted with unsubstituted alkyl, alkylene substituted with unsubstituted aryl;
- $R^3$ is selected from the group consisting of halosubstituted alkyl, unsubstituted cycloalkyl, halosubstituted or unsubstituted heteroaryl, vinyl, C(O)H, —C(O)$R^{12}$, C(O)NH$R^{14}$, and —OR$^{10}$ wherein
- $R^{10}$ is selected from the group consisting of unsubstituted alkyl, and unsubstituted heterocycloalkyl;
- $R^{12}$ is unsubstituted alkyl; and
- $R^{14}$ is selected from the group consisting of H, unsubstituted alkyl, substituted aryl, substituted and unsubstituted arylalkyl and unsubstituted cycloalkyl.

2. The compound of claim 1, or a salt, hydrate, or solvate thereof, wherein $R^3$ is —C(O)$R^{12}$ and $R^2$ is unsubstituted linear alkylene and $R^{12}$ is unsubstituted alkyl.

3. The compound of claim 1, or a salt, hydrate, or solvate thereof, wherein $R^3$ is —C(O)$R^{12}$ and $R^2$ is methylene and $R^{12}$ is unsubstituted alkyl.

4. The compound of claim 1, or a salt, hydrate, or solvate thereof, wherein the compound has the following structure:

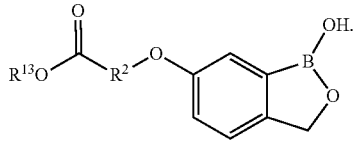

5. The compound of claim 4, or a salt, hydrate, or solvate thereof, wherein $R^{12}$ is methyl or ethyl or unsubstituted $C_3$ alkyl or unsubstituted $C_4$ alkyl or unsubstituted $C_5$ alkyl or unsubstituted $C_6$ alkyl.

6. The compound of claim 4, or a salt, hydrate, or solvate thereof, wherein $R^2$ is methylene or ethylene or propylene or butylene or pentylene or hexylene.

7. The compound of claim 4, or a salt, hydrate, or solvate thereof, wherein $R^2$ is methylene and $R^{12}$ is methyl or ethyl or unsubstituted $C_3$ alkyl or unsubstituted $C_4$ alkyl.

8. The compound of claim 4, or a salt, hydrate, or solvate thereof, wherein $R^2$ is ethylene and $R^{12}$ is methyl or ethyl or unsubstituted $C_3$ alkyl or unsubstituted $C_4$ alkyl.

9. The compound of claim 4, or a salt, hydrate, or solvate thereof, wherein $R^2$ is propylene and $R^{12}$ is methyl or ethyl or unsubstituted $C_3$ alkyl or unsubstituted $C_4$ alkyl.

10. The compound of claim 1, or a salt, hydrate, or solvate thereof, wherein the compound has the following structure:

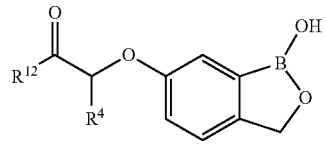

wherein $R^4$ is $C_1$-$C_6$ unsubstituted alkyl.

11. The compound of claim 10, or a salt, hydrate, or solvate thereof, wherein $R^{12}$ is methyl or ethyl or unsubstituted $C_3$ alkyl or unsubstituted $C_4$ alkyl or unsubstituted $C_5$ alkyl or unsubstituted $C_6$ alkyl.

12. The compound of claim 10, or a salt, hydrate, or solvate thereof, wherein $R^4$ is methyl or ethyl or unsubstituted $C_3$ alkyl or unsubstituted $C_4$ alkyl or unsubstituted $C_5$ alkyl or unsubstituted $C_6$ alkyl.

13. The compound of claim 10, or a salt, hydrate, or solvate thereof, wherein $R^4$ is methyl and $R^{12}$ is methyl or ethyl or unsubstituted $C_3$ alkyl or unsubstituted $C_4$ alkyl.

14. The compound of claim 10, or a salt, hydrate, or solvate thereof, wherein $R^4$ is methyl and $R^{12}$ is methyl.

15. The compound of claim 10, or a salt, hydrate, or solvate thereof, wherein $R^4$ is ethyl and $R^{12}$ is methyl or ethyl or unsubstituted $C_3$ alkyl or unsubstituted $C_4$ alkyl.

16. The compound of claim 10, or a salt, hydrate, or solvate thereof, wherein $R^4$ is propyl and $R^{12}$ is methyl or ethyl or unsubstituted $C_3$ alkyl or unsubstituted $C_4$ alkyl.

17. The compound of claim 10, or a salt, hydrate, or solvate thereof, wherein $R^4$ is isopropyl and $R^{12}$ is methyl or ethyl or unsubstituted $C_3$ alkyl or unsubstituted $C_4$ alkyl.

18. The compound of claim 1, or a salt, hydrate, or solvate thereof, wherein the compound has the following structure:

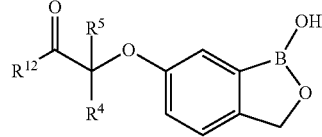

wherein $R^4$ is $C_1$-$C_6$ unsubstituted alkyl and $R^5$ is $C_1$-$C_6$ unsubstituted alkyl.

19. The compound of claim 18, or a salt, hydrate, or solvate thereof, wherein $R^{12}$ is methyl or ethyl or unsubstituted $C_3$ alkyl.

20. The compound of claim 18, or a salt, hydrate, or solvate thereof, wherein $R^4$ is methyl, and $R^{12}$ is methyl or ethyl or unsubstituted $C_3$ alkyl or unsubstituted $C_4$ alkyl or unsubstituted $C_5$ alkyl or unsubstituted $C_6$ alkyl.

21. The compound of claim 18, or a salt, hydrate, or solvate thereof, wherein $R^4$ is ethyl, and $R^{12}$ is methyl or ethyl or unsubstituted $C_3$ alkyl or unsubstituted $C_4$ alkyl or unsubstituted $C_5$ alkyl or unsubstituted $C_6$ alkyl.

22. The compound of claim 18, or a salt, hydrate, or solvate thereof, wherein $R^4$ is unsubstituted $C_3$ alkyl, and $R^{12}$ is methyl or ethyl or unsubstituted $C_3$ alkyl or unsubstituted $C_4$ alkyl or unsubstituted $C_5$ alkyl or unsubstituted $C_6$ alkyl.

23. The compound of claim 18, or a salt, hydrate, or solvate thereof, wherein $R^4$ is methyl, $R^5$ is methyl and $R^{12}$ is methyl or ethyl or unsubstituted $C_3$ alkyl of unsubstituted $C_4$ alkyl or unsubstituted $C_5$ alkyl or unsubstituted $C_6$ alkyl.

24. The compound of claim 18, or a salt, hydrate, or solvate thereof, wherein $R^4$ is methyl, $R^5$ is methyl and $R^{12}$ is methyl or ethyl or unsubstituted $C_3$ alkyl.

25. The compound of claim 18, or a salt, hydrate, or solvate thereof, wherein $R^4$ is ethyl, $R^5$ is ethyl and $R^{12}$ is methyl or ethyl or unsubstituted $C_3$ alkyl or unsubstituted $C_4$ alkyl or unsubstituted $C_5$ alkyl or unsubstituted $C_6$ alkyl.

26. The compound of claim 1, or a salt, hydrate, or solvate thereof, which is methyl [2-(1,3-dihydro-1-hydroxy-2,1-benzoxaborol-6-yloxy)]acetamide, ethyl [2-(1,3-dihydro-1-hydroxy-2,1-benzoxaborol-6-yloxy)]acetamide, N-propyl-2-(1,3-dihydro-1-hydroxy-2,1-benzoxaborol-6-yloxy) acetamide, N-tert-butyl-2-(1,3-dihydro-1-hydroxy-2,1-benzoxaborol-6-yloxy)acetamide, or N-(2,6-dimethylphenyl)-[2-(1,3-dihydro-1-hydroxy-2,1-benzoxaborol-6-yloxy)]acetamide.

27. The compound of claim 4, or a salt, hydrate, or solvate thereof, which is 1-(1,3-dihydro-1-hydroxy-2,1-benzoxaborol-6-yloxy) butan-2-one, 1-(1,3-dihydro-1-hydroxy-2,1-benzoxaborol-6-yloxy) pentan-2-one, 1-(1,3-dihydro-1-hydroxy-2,1-benzoxaborol-6-yloxy)-4-methylpentan-2-one, 3-(1,3-dihydro-1-hydroxy-2,1-benzoxaborol-6-yloxy) butan-2-one, 2-(1,3-dihydro-1-hydroxy-2,1-benzoxaborol-6-yloxy) pentan-3-one, 3-(1,3-dihydro-1-hydroxy-2,1-benzoxaborol-6-yloxy) pentan-2-one, 3-(1,3-dihydro-1-hydroxy-2,1-benzoxaborol-6-yloxy) hexan-2-one, 3-(1,3-dihydro-1-hydroxy-2,1-benzoxaborol-6-yloxy) heptan-4-one, 3-(1,3-dihydro-1-hydroxy-2,1-benzoxaborol-6-yloxy)-4-methyl-pentan-2-one, 3-(1,3-dihydro-1-hydroxyl-2,1-benzoxaborol-6-yloxy)-3-methylbutan-2-one, or 6-(2-hydroxy-1-methylbutoxy)-1,3-dihydro-1-hydroxy-2,1-benzoxaborole.

28. The compound of claim 1, or a salt, hydrate, or solvate thereof, which is 6-((2'-chloro)thiazol-5-yl)methoxy-1,3-dihydro-1-hydroxy-2,1-benzoxaborole, 6-((3,5-dimethylisoxazol-4-yl)methoxy)-1,3-dihydro-1-hydroxy-2,1-benzoxaborole, 6-((isoindoline-1,3-dione-2-yl)propoxy)-1,3-dihydro-1-hydroxy-2,1-benzoxaborole, 6-(2-(1H-tetrazol-5-yl)oxymethyl)benzo[c][1,2]oxaborol-1(3H)-ol, 2-(1-hydroxy-1,3-dihydrobenzo[c][1,2]oxaborol-6-yloxy)-N-(cyclopropylsulfonyl) acetamide, 5-(1-hydroxy-1,3-dihydrobenzo[c][1,2]oxaborol-6-yloxy)thiazolidine-2,4-dione, 5-((1-hydroxy-1,3-dihydrobenzo[c][1,2]oxaborol-6-yloxy)methyl)thiazolidine-2,4-dione, or 5-(2-(1-hydroxy-1,3-dihydrobenzo[c][1,2]oxaborol-6-yloxy)ethyl)thiazolidine-2,4-dione.

29. The compound of claim 1, or a salt, hydrate, or solvate thereof, which is [2-(1,3-dihydro-1-hydroxy-2,1-benzoxaborol-6-yloxy)]acetic acid, methyl [2-(1,3-dihydro-1-hydroxy-2,1-benzoxaborol-6-yloxy)]acetate, ethyl [2-(1,3-dihydro-1-hydroxy-2,1-benzoxaborol-6-yloxy)]acetate, tert-butyl [2-(1,3-dihydro-1-hydroxy-2,1-benzoxaborol-6-yloxy)]acetate, [2-(1,3-dihydro-1-hydroxy-2,1-benzoxaborol-6-yloxy)]acetaldehyde, ethyl [2-(1,3-dihydro-1-hydroxy-2,1-benzoxaborol-6-yloxy)] propanoate, ethyl [2-(1,3-dihydro-1-hydroxy-2,1-benzoxaborol-6-yloxy)] butanoate, ethyl [2-(1,3-dihydro-1-hydroxy-2,1-benzoxaborol-6-yloxy)]-2-methylpropanoate, ethyl [2-(1,3-dihydro-1-hydroxy-2,1-benzoxaborol-6-yloxy)]-2-phenylacetate, [3-(1,3-dihydro-1-hydroxy-2,1-benzoxaborol-6-yloxy)]propanoic acid, [4-(1,3-dihydro-1-hydroxy-2,1-benzoxaborol-6-yloxy]butanoic acid, [5-(1,3-dihydro-1-hydroxy-2,1-benzoxaborol-6-yloxy]pentanoic acid, [2-(1,3-dihydro-1-hydroxy-2,1-benzoxaborol-6-yloxy)]propanoic acid, [2-(1,3-dihydro-1-hydroxy-2,1-benzoxaborol-6-yloxy) ]butanoic acid, [2-(1,3-dihydro-1-hydroxy-2,1-benzoxaborol-6-yloxy)]-2-methylpropanoic acid, or [2-(1,3-dihydro-1-hydroxy-2,1-benzoxaborol-6-yloxy)]-2-phenylacetic acid.

30. A combination comprising the compound of claim 1, or a salt thereof, together with at least one other therapeutically active agent.

31. A pharmaceutical formulation comprising:
   a) the compound of claim 1, or a pharmaceutically acceptable salt thereof; and
   b) a pharmaceutically acceptable excipient.

32. The pharmaceutical formulation of claim 31, wherein the pharmaceutical formulation is a unit dosage form.

* * * * *